(12) United States Patent
Le Gall et al.

(10) Patent No.: US 9,226,962 B2
(45) Date of Patent: Jan. 5, 2016

(54) HUMAN CD3-SPECIFIC ANTIBODY WITH IMMUNOSUPPRESSIVE PROPERTIES

(71) Applicant: Affimed Therapeutics, AG, Heidelberg (DE)

(72) Inventors: Fabrice Le Gall, Edingen-Neckarhausen (DE); Sergey Kipriyanov, Heidelberg (DE); Melvin Little, Neckargemund (DE); Uwe Reusch, Maikammer (DE)

(73) Assignee: AFFIMED GMBH, Heidelberg (DE)

( * ) Notice: Subject to any disclaimer, the term of this patent is extended or adjusted under 35 U.S.C. 154(b) by 503 days.

(21) Appl. No.: 13/739,736

(22) Filed: Jan. 11, 2013

(65) Prior Publication Data

US 2013/0115213 A1 May 9, 2013

Related U.S. Application Data

(62) Division of application No. 10/527,346, filed as application No. PCT/EP03/10064 on Sep. 10, 2003, now abandoned.

(30) Foreign Application Priority Data

Sep. 10, 2002 (EP) .................................... 02020236

(51) Int. Cl.
*A61K 39/00* (2006.01)
*A61K 39/395* (2006.01)
*C07K 16/28* (2006.01)

(52) U.S. Cl.
CPC ......... *A61K 39/3955* (2013.01); *C07K 16/2809* (2013.01); *A61K 2039/505* (2013.01); *C07K 2317/34* (2013.01); *C07K 2317/622* (2013.01); *C07K 2317/626* (2013.01); *C07K 2317/73* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,837,242 | A | 11/1998 | Holliger et al. |
| 7,122,646 | B2 | 10/2006 | Holliger et al. |
| 7,129,330 | B1 | 10/2006 | Little et al. |
| 2002/0142000 | A1 | 10/2002 | Digan et al. |

FOREIGN PATENT DOCUMENTS

| | | |
|---|---|---|
| EP | 0952218 A2 | 10/1999 |
| WO | WO 9847531 A2 | 10/1998 |
| WO | WO 99/57150 | 11/1999 |
| WO | WO 00/02520 | 1/2000 |
| WO | WO 00/05268 | 2/2000 |
| WO | WO 01/087982 | 11/2001 |

OTHER PUBLICATIONS

Rule 132 Declaratoin Dr. Melvyn Little, filed Aug. 27, 2010 in connection with U.S. Appl. No. 10/527,346, 7 pages in total.*
Rule 132 Declaratoin Dr. Melvyn Little, filed Dec. 13, 2011 in connection with U.S. Appl. No. 10/527,346, 7 pages in total.*
Holliger et al., Protein Engineering, vol. 9 No. 3 pp. 299-305, 1996.*
"Commonly Used Reagents and Equipment"; Current Protocols in Immunology; pp. A.2A.1-A.2A.8 (1999).
Biddison, et al.; "Measurement of Polyclonal and Antigen-Specific Cytotoxic T Cell Function"; Current Protocols in Immunology; Supplement 17, pp. 7.17.1-7.17.14 (1996).
Bitter, et al., "Expression and Secretion Vectors for Yeast," Methods Enzymol.; 153:516-544 (1987).
Bothmann and Pluckthun, "Selection for a periplasmic factor improving phage display and functional oeriolasmic expression" Nat. Biotechnol.; 16:376-380 (1998).
Bradford, A Rapid and Sensitive Method for the Quantitation of the Microgram Quantities of Protein Utilizing the Principle of Protein-Dye Binding, Anal. Biochem.; 12:248-254 (1976).
Broglie, R., et al., "Light-Regulated Expression of a Pea Ribulos-1,5-Bisphoshate Carboxylase Small Subunit Gene in Transformed Plant Cells," Science; 224:838-843 (1984).
Chapman, et al.; "Therapeutic Antibody Fragments with Prolonged in Vivo Half-Lives"; Nature Biotechnology; vol. 17, No. 8, pp. 780-783 (Aug. 1999).
Cochlovius, et al., "Treatment of Human B Cell Lymphoma Xenographs with a CD3 x CD19 Diabodv and T Calls," J. Immun.; 165:888-895 (2000).
Colbere-Garapin, et al., "A New Dominant Hybrid Selective Marker for Higher Eukaryotic Cells," J. Mol. Biol.; 150:1-4 (1981).
Cole, M.S., et al., "Human IgG2 Variants of Chimeric Anti-DC3 Are Nonmitogenic to T Cells," J. Immunol.; 159:3613-3621 (1997).
Colman; "Effects of Amino Acid Sequence Changes on Antibody-Antigen Interactions"; Research in Immunology; vol. 145, pp. 33-36 (1994).
Coruzzi, G., et al., "Tissue-specific and light-regulated expression of a pea nuclear gene encoding the small subunit of ribulose-1,5-biophosohate carboxylase" EMBO J.; 3:1671-1680 (1984).
Encylopedia Britannica; "Sterile Medicament"; Encyclopedia Britannica, Inc.; pp. 1-2 (1995).

(Continued)

*Primary Examiner* — Zachary Skelding
(74) *Attorney, Agent, or Firm* — Perkins Coie LLP; Viola T. Kung

(57) ABSTRACT

Described are mono- and multivalent scFv-antibodies comprising the binding sites specific for the human T cell marker CD3. These antibodies are strongly immunosuppressive and do not cause a significant release of cytokines. Furthermore, polynucleotides encoding said antibodies are described as well as vectors comprising said polynucleotides, host cells transformed therewith and their use in the production of said antibodies. Pharmaceutical compositions containing any of the above mentioned polynucleotides, antibodies or vectors are useful for immunotherapy, preferably against acute transplant rejections.

6 Claims, 19 Drawing Sheets

(56) References Cited

OTHER PUBLICATIONS

Engelhard, et al., "The insect tracheal system: A conduit for the systemic spread of Autographa californica M nuclear polyhedrosis virus" Proc. Natl. Acad. Sci.; 91:3224-3227 (1994).
Hartman and Mulligan, "Two dominant-acting selectable markers for gene transfer studies in mammalian cells" Proc. Natl. Acad. Sci.; 85:8047-8051.
Hobbs, S. or Murry, L.E. in McGraw Hill Yearbook of Science and Technology (1992) McGraw Hill, New York, N.Y.: pp. 189-196.
Holck and Kleppe, "Cloning and sequencing of the gene for the DNA-binding 17K protein of *Escherichia coli*" Gene; 67:117-124 (1988).
Holliger, et al.; "Carcinoembryonic Antigen (CEA)-specific T-Cell Activation in Colon Carcinoma Induced by Anti-CD3xAnti-CEA Bispecific Diabodies and B7xAnti-CEA Bispecific Fusion Proteins"; Cancer Research; vol. 59, pp. 2909-2916 (1999).
Horn, "High volumetric yields of functional dimeric miniantibodies in *Escherichia coli*, using an optimized expression vector and high-cell-density fermentation under non-limited growth conditions" Appl. Microbiol. Biotechnol.; 46:524-532 (1996).
Hornbeck; "Assays for Antibody Production"; Current Protocols in Immunology; pp. 2.1.1-2.1.22 (1991).
Hsu, et al.; "A Humanized Anti-CD3 Antibody, HuM291, With Low Mitogenic Activity, Mediates Complete and Reversible T-Cell Depletion in Chimpanzees"; Transplantation; vol. 68, No. 4, pp. 545-554 (Aug. 27, 1999).
International Search Report of International Application No. PCT/EP03/10064 with a mailing date of Dec. 12, 2003.
Kipriyanov, et al., "Bispecific CD3 x CD19 Diabody for T Cell-Midiated Lysis of Malignant Human B Cells" Int. J. Cancer; 77:763-772 (1998).
Kipriyanov, et al., "Two amino acid mutations in an anti-human CD3 single chain Fv antibody fragment that affect the yield on bacterial secretion but not the affinity," Protein Engineer; 10:445-453 (1997).
Logan and Shenk, "Adenovirus tripartite leader sequence enhances translation of MRNAs late after infection" Proc. Natl. Acad. Sci.; 81:3655-3659 (1984).
Lowy, I. et al., ""Isolation of Transforming DNA: Cloning the Hamster aprt Gene,"" Cell; 22:817-823 (1980).
MacCallum, et al.; "Antibody-Antigen Interactions: Contact Analysis and Binding Site Topography"; Journal of Molecular Biology; vol. 262, pp. 732-745 (1996).
Marks, et al., "By-passing Immunization: Building High Affinity Human Antibodies by Chain Shuffling," Biotechnology; 10:779-783 (1997).
Maurer, et al., "Gene Regulation at the Right Operator (OR) of Bacteriophage A," J. Mol. Biol. 139:147-161 (1980).
Mersmann, et al., "Monitoring of scFv selected by phage display using detection of scFv-pill fusion proteins in a microtiter scale assay" J. Immunol.; 200:51-62 (1996).
Mottram, P. L., et al., "New Anti-CD3 Agents for Transplantation Tolerance Induction," Drugs of the Future; 23(10):1091-1098 (1998).
Rhodes, C.A., et al., "Transformation of Maize by Electroporation of Embroyos," Methods Mol. Biol.; 55:121-131 (1995).
Rudikoff, et al.; "Single Amino Acid Substitution Altering Antigen-Binding Specificity"; Proceedings of the National Academy of Sciences of the United States of America; vol. 79, pp. 1979-1983 (Mar. 1982).
Salmeron, et al.; "A Conformational Epitope Expressed Upon Association of CD3-e With Either CD3-d or CD3-y is the Main Target for Recognition by Anti-CD3 Monoclonal Antibodies"; The Journal of Immunology; vol. 147, No. 9, pp. 3047-3052 (Nov. 1, 1991).
Sambrook, et al.; Molecular Cloning, Cold Spring Harbor Laboratory Press (1989).
Scharf, et al., "Heat Stress Promoters and Transcription Factors," Springer-Verlag Berlin Heidelberg; 125-162 (1994).
Shen, et al.; "Fiber Coating With Surfactant Solutions"; Physics of Fluids; vol. 14, No. 11, pp. 4055-4068 (Nov. 2002).
Sheriff; et al.; "Comparison of CH1 Domains in Different Classes of Murine Antibodies"; Journal of Molecular Biology; vol. 263, pp. 385-389 (1996).
Takamatsu, et al., "Expression of bacterial chloramphenicol aetyltransferase gene in tobacco plants mediated by TMV-RNA" EMBO J.; 6(2):307-311 (1987).
Thisted, et al. "Mechanism of post-segregational killing: Sok Antisense RNA interacts with Hok mRNA via its 5'-end single-stranded leader and competes with the 3'-end of Hok mRNA for binding to the mok translational initiation region," EMBO J.; 13(8):1960-1968 (1994).
Wigler, et al., "Transfer of Purified Herpes Virus Thymidine Kinase Gene to Cultured Mouse Cells," Cell; 11:223-232 (1977).
Wigler, et al., "Transformation of mammalian cells with an amplifiable dominant-acting gene," Proc. Natl. Acad. Sci.; 77(6):3567-3570 (1980).
Winter, J., et al. "The Expression of Heat Shock Protein and Cognate Genes During Plant Development," Results Probl. Cell Differ.; 17:85-105 (1991).
Woodle, et al.; "OKT3 F(AB')2 Fragments—Retention of the Immunosuppressive Properties of Whole Antibody With marked Reduction in T Cell Activation and Lymphokine Release"; Transplantation; vol. 52, No. 2, pp. 354-360 (Aug. 1991).

\* cited by examiner scFv, 30 kDa   Diabody, 60 kDa (scFv)₂, 60 kDa   scDb, 60 kDa scFv₁₀     ...L T V S S A K T T P K L G G D I V L...

scFv₆     ...L T V S S A K T T P        D I V L...

Sequence Listing

<110> Affimed Therapeutics AG

<120> Human CD3-specific antibody with immunosuppressive properties

<130> A 3040EP

<140>
<141>

<160> 2 a:

<210> 1
<211> 6091
<212> DNA
<213> Artificial Seqence

<220>
<223> Description of the Artificial Sequence: pSKK3 scFv6 anti-CD3

<400> 1 :
acccgacacc atcgaatggc gcaaaaacctt tcgcggtatg gcatgatagc gcccggaaga    60
gagtcaattc agggtggtga atgtgaaacc agtaacgtta tacgatgtcg cagagtatgc    120
cggtgtctct tatcagaccg tttcccgcgt ggtgaaccag gccagccacg tttctgcgaa    180
aacgcgggaa aaagtggaag cggcgatggc ggagctgaat tacattccca accgggtggc    240
acaacaactg gcgggcaaac agtcgttgct gattggcgtt gccacctcca gtctggccct    300
gcacgcgccg tcgcaaattg tcgcggcgat taaatctcgc gccgatcaac tgggtgccag    360
cgtggtggtg tcgatggtag aacgaagcgg cgtcgaagcc tgtaaagcgg cggtgcacaa    420
tcttctcgcg caacgcgtca gtgggctgat cattaactat ccgctggatg accaggatgc    480
cattgctgtg gaagctgcct gcactaatgt tccggcgtta tttcttgatg tctctgacca    540
gacacccatc aacagtatta tttctccca tgaagacggt acgcgactgg gcgtggagca    600
tctggtcgca ttgggtcacc agcaaatcgc gctgttagcg ggcccattaa gttctgtctc    660
ggcgcgtctg cgtctggctg gctggcataa atatctcact cgcaatcaaa ttcagccgat    720
agcggaacgg gaaggcgact ggagtgccat gtccggtttt caacaaacca tgcaaatgct    780
gaatgagggc atcgttccca ctgcgatgct ggttgccaac gatcagatgg cgctgggcgc    840
aatgcgcgcc attaccgagt ccgggctgcg cgttggtgcg gatatctcgg tagtgggata    900

FIGURE 15 - 1 cgacgatacc gaagacagct catgttatat cccgccgtta accaccatca aacaggattt    960
tcgcctgctg gggcaaacca gcgtggaccg cttgctgcaa ctctctcagg gccaggcggt   1020
gaagggcaat cagctgttgc ccgtctcact ggtgaaaaga aaaccaccc tggcgcccaa   1080 tacgcaaacc gcctctcccc gcgcgttggc cgattcatta atgcagctgg cacgacaggt   1140
ttcccgactg gaaagcgggc agtgagcggt acccgataaa agcggcttcc tgacaggagg   1200 ccgtttgtt ttgcagccca cctcaacgca attaatgtga gttagctcac tcattaggca   1260
ccccaggctt tacactttat gcttccggct cgtatgttgt gtggaattgt gagcggataa   1320
caatttcaca caggaaacag ctatgaccat gattacgaat ttctgaagaa ggagatatac   1380
atatgaaata cctattgcct acggcagccg ctggcttgct gctgctggca gctcagccgg   1440
ccatggcgca ggtgcagctg cagcagtctg gggctgaact ggcaagacct ggggcctcag   1500
tgaagatgtc ctgcaaggct tctggctaca cctttactag gtacacgatg cactgggtaa   1560
aacagaggcc tggacagggt ctggaatgga ttggatacat taatcctagc cgtggttata   1620
ctaattacaa tcagaagttc aaggacaagg ccacattgac tacagacaaa tcctccagca   1680
cagcctacat gcaactgagc agcctgacat ctgaggactc tgcagtctat tactgtgcaa   1740
gatattatga tgatcattac agccttgact actggggcca aggcaccact ctcacagtct   1800
cctcagccaa acaacaccc gatatcgtgc tcactcagtc tccagcaatc atgtctgcat   1860
ctccagggga gaaggtcacc atgacctgca gtgccagctc aagtgtaagt tacatgaact   1920
ggtaccagca gaagtcaggc acctccccca aaagatggat ttatgacaca tccaaactgg   1980
cttctggagt ccctgctcac ttcaggggca gtgggtctgg gacctcttac tctctcacaa   2040
tcagcggcat ggaggctgaa gatgctgcca cttattactg ccagcagtgg agtagtaacc   2100
cattcacgtt cggctcgggg acaaagttgg aaataaaccg ggctgatact gcggccgctg   2160
gatcccatca ccatcaccat cactaatcta gaggcctgtg ctaacttaag aaggagatat   2220
acatatgaaa aagtggttat tagctgcagg tctcggttta gcactggcaa cttctgctca   2280
ggcggctgac aaaattgcaa tcgtcaacat gggcagcctg ttccagcagg tagcgcagaa   2340
aaccggtgtt tctaacacgc tggaaaatga gttcaaaggc cgtgccagcg aactgcagcg   2400
tatggaaacc gatctgcagg ctaaaatgaa aaagctgcag tccatgaaag cgggcagcga   2460
tcgcactaag ctggaaaaag acgtgatggc tcagcgcag acttttgctc agaaagcgca   2520 ggctttgag caggatcgcg cacgtcgttc caacgaagaa cgcggcaaac tggttactcg   2580
tatccagact gctgtgaaac ccgttgccaa cagccaggat atcgatctgg ttgttgatgc   2640
aaacgccgtt gcttacaaca gcagcgatgt aaaagacatc actgtcgacg tactgaaaca   2700
ggttaaataa tgctcgagga actgctgaaa catctgaagg agctgcttaa aggtgagttc   2760

FIGURE 15 - 2 tgataagctt gacctgtgaa gtgaaaaatg gcgcacattg tgcgacattt ttttgtctg 2820 ccgtttaccg ctactgcgtc acggatccgg ccgaacaaac tccgggaggc agcgtgatgc 2880
ggcaacaatc acacggattt cccgtgaacg gtctgaatga gcggattatt ttcagggaaa 2940
gtgagtgtgg tcagcgtgca ggtatatggg ctatgatgtg cccggcgctt gaggctttct 3000
gcctcatgac gtgaaggtgg tttgttgccg tgttgtgtgg cagaaagaag atagccccgt 3060
agtaagttaa ttttcattaa ccaccacgag gcatccctat gctagtcca catcaggata 3120 gcctcttacc gcgctttgcg caaggagaag aaggccatga aactaccacg aagttccctt 3180
gtctggtgtg tgttgatcgt gtgtctcaca ctgttgatat tcacttatct gacacgaaaa 3240
tcgctgtgcg agattcgtta cagagacgga cacagggagg tgcggcttt catggcttac 3300 gaatccggta agtagcaacc tagaggcggg cgcaggcccg cctttcagg actgatgctg 3360 gtctgactac tgaagcgcct ttataaaggg gctgctggtt cgccggtagc ccctttctcc 3420
ttgctgatgt tgtgggaatt tcgagcaaga cgtttcccgt tgaatatggc tcataacacc 3480
ccttgtatta ctgtttatgt aagcagacag ttttattgtt catgatgata tattttate 3540 ttgtgcaatg taacatcaga gattttgaga cacaacgtgg ctttcccccc cccccctgca 3600
gggggggggg ggcgctgagg tctgcctcgt gaagaaggtg ttgctgactc ataccaggcc 3660
tgaatcgccc catcatccag ccagaaagtg agggagccac ggttgatgag agctttgttg 3720
taggtggacc agttggtgat tttgaacttt tgctttgcca cggaacggtc tgcgttgtcg 3780
ggaagatgcg tgatctgggg atccccacgc gccctgtagc ggcgcattaa gcgcggcggg 3840
tgtggtggtt acgcgcagcg tgaccgctac acttgccagc gccctagcgc ccgctccttt 3900
cgctttcttc cctttcttttc tcgccacgtt cgccggcttt ccccgtcaag ctctaaatcg 3960
gggcatccct ttagggttcc gatttagtgc tttacggcac ctcgaccccca aaaaacttga 4020 ttagggtgat ggttcacgta gtgggccatc gccctgatag acggttttc gccctttgac 4080 gttggagtcc acgttcttta atagtggact cttgttccaa actggaacaa cactcaaccc 4140
tatctcggtc tattcttttg atttataagg gattttgccg atttcggcct attggttaaa 4200
aaatgagctg atttaacaaa aatttaacgc gaattttaac aaaatattaa cgtttacaat 4260
ttcaggtggc gaattcccccg gggaattcac tttcggggga aatgtgcgcg gaacccctat 4320
ttgtttattt tctaaatac attcaaatat gtatccgctc atgagacaat aaccctgata 4380
aatgcttcaa taatattgaa aaaggaagag tatgagtatt caacatttcc gtgtcgccct 4440
tattcccttt tttgcggcat tttgccttcc tgtttttgct cacccagaaa cgctggtgaa 4500
agtaaaagat gctgaagatc agttgggtgc acgagtgggt tacatcgaac tggatctcaa 4560
cagcggtaag atccttgaga gttttcgccc cgaagaacgt tttccaatga tgagcacttt 4620

FIGURE 15 - 3

```
taaagttctg ctatgtggcg cggtattatc ccctattgac gccgggcaag agcaactcgg   4680
tcgccgcata cactattctc agaatgactt ggttgagtac tcaccagtca cagaaaagca   4740
tcttacggat ggcatgacag taagagaatt atgcagtgct gccataacca tgagtgataa   4800
cactgcggcc aacttacttc tgacaacgat cggaggaccg aaggagctaa ccgcttttt   4860 gcacaacatg ggggatcatg taactcgcct tgatcgttgg gaaccggagc tgaatgaagc   4920
cataccaaac gacgagcgtg acaccacgat gcctgtagca atggcaacaa cgttgcgcaa   4980
actattaact ggcgaactac ttactctagc ttcccggcaa caattaatag actggatgga   5040
ggcggataaa gttgcaggac cacttctgcg ctcggccctt ccggctggct ggtttattgc   5100
tgataaatct ggagccggtg agcgtgggtc tcgcggtatc attgcagcac tggggccaga   5160
tggtaagccc tcccgtatcg tagttatcta cacgacgggg agtcaggcaa ctatggatga   5220
acgaaataga cagatcgctg agataggtgc ctcactgatt aagcattggt aactgtcaga   5280
ccaagtttac tcatatatac tttagattga tttaaaactt catttttaat ttaaaaggat   5340
ctaggtgaag atcctttttg ataatctcat gaccaaaatc ccttaacgtg agttttcgtt   5400
ccactgagcg tcagaccccg tagaaaagat caaaggatct tcttgagatc ctttttttct   5460
gcgcgtaatc tgctgcttgc aaacaaaaaa accaccgcta ccagcggtgg tttgtttgcc   5520
ggatcaagag ctaccaactc tttttccgaa ggtaactggc ttcagcagag cgcagatacc   5580
aaatactgtc cttctagtgt agccgtagtt aggccaccac ttcaagaact ctgtagcacc   5640
gcctacatac ctcgctctgc taatcctgtt accagtggct gctgccagtg gcgataagtc   5700
gtgtcttacc gggttggact caagacgata gttaccggat aaggcgcagc ggtcgggctg   5760
aacggggggt tcgtgcacac agcccagctt ggagcgaacg acctacaccg aactgagata   5820
cctacagcgt gagctatgag aaagcgccac gcttcccgaa gggagaaagg cggacaggta   5880
tccggtaagc ggcagggtcg gaacaggaga gcgcacgagg gagcttccag ggggaaacgc   5940
ctggtatctt tatagtcctg tcgggtttcg ccacctctga cttgagcgtc gatttttgtg   6000
atgctcgtca ggggggcgga gcctatggaa aaacgccagc aacgcggcct ttttacggtt   6060
cctggccttt tgctggcctt ttgctcacat g                                  6091
``` b:

<210> 2
<211> 267
<212> PRT
<213> Artificial Sequence

<220>

<223> Description of the Artificial Sequence: scFv6 anti-CD3

<400> 2

| | |
|---|---|
| MKYLLPTAAAGLLLLAAQPA MAQVQLQQSGAELARPGASV KMSCKASGYT FTRYTMHWVK | 60 |
| QRPGQGLEWI GYINPSRGYT NYNQKFKDKA TLTTDKSSST AYMQLSSLTS EDSAVYYCAR | 120 |
| YYDDHYSLDY WGQGTTLTVS SAKTTPDIVL TQSPAIMSAS PGEKVTMTCS ASSSVSYMNW | 180 |
| YQQKSGTSPK RWIYDTSKLASGVPAHFRGS GSGTSYSLTI SGMEAEDAAT YYCQQWSSNP | 240 |
| FTFGSGTKLE INRADTAAAG SHHHHHH | 267 |

FIGURE 15 - 5

HUMAN CD3-SPECIFIC ANTIBODY WITH IMMUNOSUPPRESSIVE PROPERTIES

PRIORITY CLAIM

The present application is a divisional of U.S. patent application Ser. No. 10/527,346, filed Sep. 23, 2005, which is a National Stage Application of International Application Number PCT/EP2003/010064, filed Sep. 10, 2003, which claims priority to European Application Number EP 02020236.2, filed Sep. 10, 2002, all of which are incorporated herein by reference in their entirety, including drawings.

SUMMARY

The present invention relates to mono- and multivalent scFv-antibodies comprising the binding sites specific for the human T cell marker CD3. The antibodies of the invention are strongly immunosuppressive and do not cause a significant release of cytokines. The present invention also relates to polynucleotides encoding said antibodies as well as vectors comprising said polynucleotides, host cells transformed therewith and their use in the production of said antibodies. Finally, the present invention relates to compositions, preferably pharmaceutical compositions, comprising any of the above mentioned polynucleotides, antibodies or vectors. The pharmaceutical compositions are useful for immunotherapy, preferably against acute transplant rejections.

OKT3, a murine IgG2a mAb directed against the ε-chain of the CD3 complex on human T lymphocytes (Salmeron et al., J. Immunol. 147 (1991), 3047-3052) and produced by a hybridoma with the ATCC deposit number of CRL 8001 is used to prevent tissue rejection after renal and hepatic transplantation, and provides an alternative treatment for transplant rejections that are unresponsive to corticosteroids. In vivo, administration of OKT3 induces a dramatic decrease in the number of circulating CD3$^+$cells as it down-modulates the T-cell receptor (TCR). However, adverse effects can occur during the first days of treatment. Chills and fever often follow the administration of OKT3 and patients occasionally suffer from nausea, vomiting, diarrhea, dyspnea, wheezing, and sterile meningitis. Many of these side effects have been attributed to the release of cytokines, especially from T cells. After a more prolonged period of use, many patients develop a human anti-mouse antibody (HAMA) response.

Binding of OKT3 alone is insufficient to trigger T cells. Proliferation of T cells which induces the release of cytokines like IL-2, IL-6, TNF-α and IFN-γ results from cross-linking of T cells and FcR-bearing cells. Human IgG Fc receptors (FcγRI, FcγRII, FcγRIII) are distributed on human monocytes/macrophages, B lymphocytes, NK cells and granulocytes. They all bind to the $C_H2$ region of both mouse and human IgG, differing in their affinity. The immunogenicity of such anti-CD3 Ab has been reduced by using chimeric antibodies made from the variable domains of a mouse mAb and the constant regions of a human Ab. To reduce binding to Fc receptors, Fc domains from particular classes of human IgG have been employed or mutations have been introduced into the Fc domain in the parts that bind to the Fc receptors. However, interactions of the Fc domains cannot be completely abrogated and the efficacy of the immunosuppressive activity was not increased.

Thus, the technical problem underlying the present invention was to provide means more suitable for preventing allograft rejection that overcome the disadvantages of the means of the prior art.

The solution of the said technical problem is achieved by providing the embodiments characterized in the claims. Antibodies have been constructed that are more efficient in suppressing T cell activation and proliferation by down-regulating the CD3 molecule but that do not cause a large release of cytokines, thus avoiding many of the unpleasant side-effects. These antibodies only comprise the variable immunoglobulin domains, so called $F_v$ modules by means of which undesired immune responses can be avoided. The $F_v$ module is formed by association of the immunoglobulin heavy and light chain variable domains, $V_H$ and $V_L$, respectively. Preferred embodiments of these antibodies are based only on the variable domains of the OKT3 antibody, but contain a serine instead of a cysteine at position H100A of the heavy chain (according to the Kabat numbering system). This mutation has previously been shown to improve the stability of the single chain Fv molecule (Kipriyanov et al., Protein Engineering 10 (1997), 445-453). Surprisingly, such antibodies, and in particular a bivalent antibody in a so-called diabody format, had a much greater immunosuppressive effect as measured by CD3 downregulation and inhibition of T cell proliferation in a mixed lymphocyte reaction (MLR) than the original parental OKT3 antibody and, in contrast to the parental OKT3, caused no significant release of the cytokines IFN-α and IL-2.

His$_6$: six C-terminal histidine residues; L: short peptide linker (the amino acid sequence is shown in bold) connecting the $V_H$ and $V_L$ domains (SEQ ID NOs:1, 2); leader, bacterial leader sequence (e.g. PelB leader) for secretion of recombinant product into periplasm; rbs, ribosome binding site; Stop: stop codon (TAA); $V_H$ and $V_L$: variable regions of the heavy and light chains specific to human CD3. Four C-terminal amino acids of $V_H$ domain and four N-terminal amino acids of the $V_L$ domain are underlined.

Figure 3:
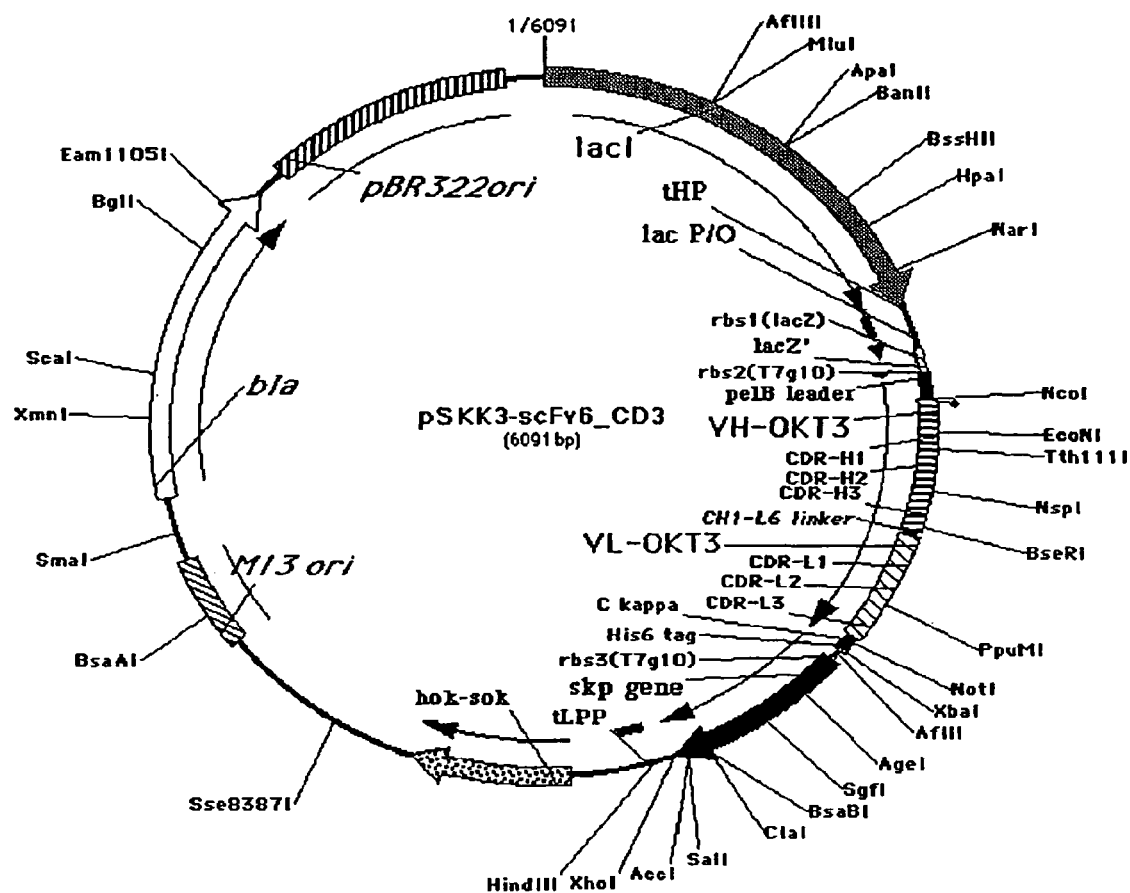

FIG. 3: Diagram of the expression plasmid pSKK3-scFv6_OKT3 bla: gene of beta-lactamase responsible for ampicillin resistance; bp: base pairs; CDR-H1, CDR-H2 and CDR-H3: sequence encoding the complementarity determining regions (CDR) 1-3 of the heavy chain; CDR-L1, CDR-L1, CDR-L2 and CDR-L3: sequence encoding the complementarity determining regions (CDR) 1-3 of the light chain; CH1-L6 linker: sequence which encodes the 6 amino acid peptide Ser-Ala-Lys-Thr-Thr-Pro connecting the $V_H$ and $V_L$ domains; His6 tag: sequence encoding six C-terminal histidine residues; hok-sok: plasmid stabilizing DNA locus; lacI: gene encoding lac-repressor; lac P/O: wild-type lac-operon promoter/operator; M13ori: intergenic region of bacteriophage M13; pBR322ori: origin of the DNA replication; PelB leader: signal peptide sequence of the bacterial pectate lyase; rbs1: ribosome binding site derived from *E. coli* lacZ gene (lacZ); rbs2 and rbs3: ribosome binding site derived from the strongly expressed gene 10 of bacteriophage T7 (T7g10); skp gene: gene encoding bacterial periplasmic factor Skp/OmpH; tHP: strong transcriptional terminator; tLPP: lipoprotein terminator of transcription; $V_H$ and $V_L$: sequence coding for the variable region of the immunoglobulin heavy and light chain, respectively. Unique restriction sites are indicated.

Figure 4:
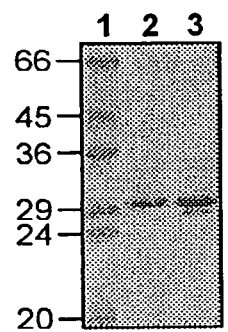

FIG. 4: Analysis of purified anti-CD3 scFv antibodies by 12% sodium dodecyl sulfate-polyacrylamide gel electrophoresis (SDS-PAGE) under reducing conditions Lane 1: $M_r$ markers (kDa, $M_r$ in thousands); Lane 2: anti-CD3 scFv$_{10}$; Lane 3: anti-CD3 scFv$_6$. The gel was stained with Coomassie Blue.

Figure 5:
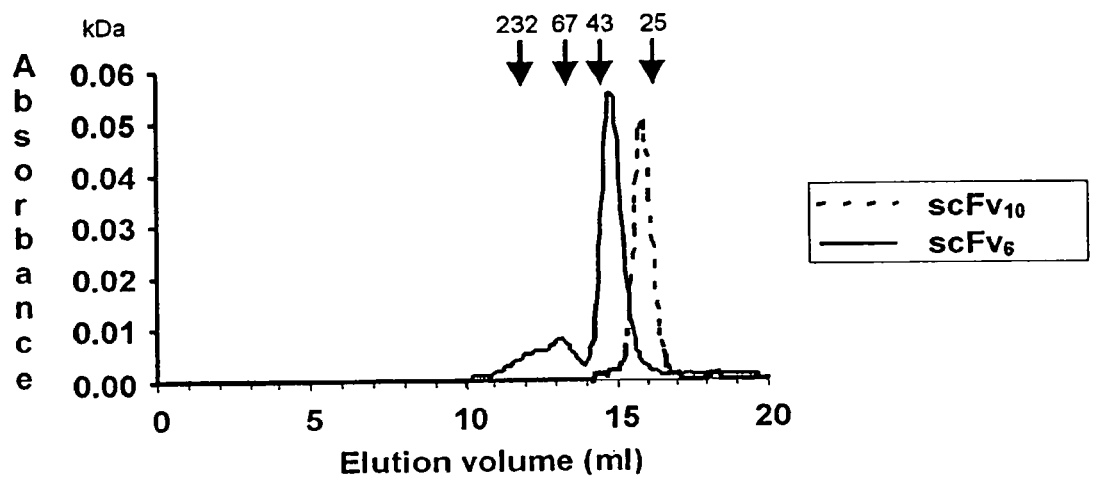

FIG. 5: Analysis of purified anti-CD3 scFv antibodies by size exclusion chromatography on a calibrated Superdex 200 column The elution positions of molecular mass standards are indicated.

Figure 6:
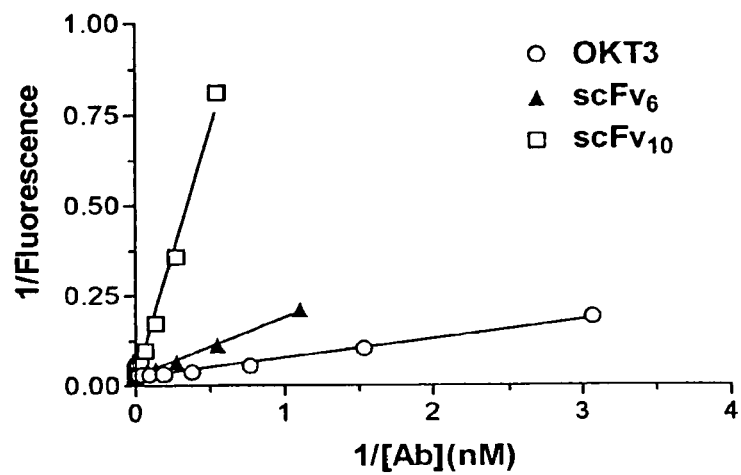

FIG. 6: Lineweaver-Burk analysis of fluorescence dependence on antibody concentration as determined by flow cytometry Binding of mAb OKT3 (circles), scFv$_6$ (triangles) and scFv$_{10}$ (squares) to CD3$^+$ Jurkat cells was measured.

Figure 7:
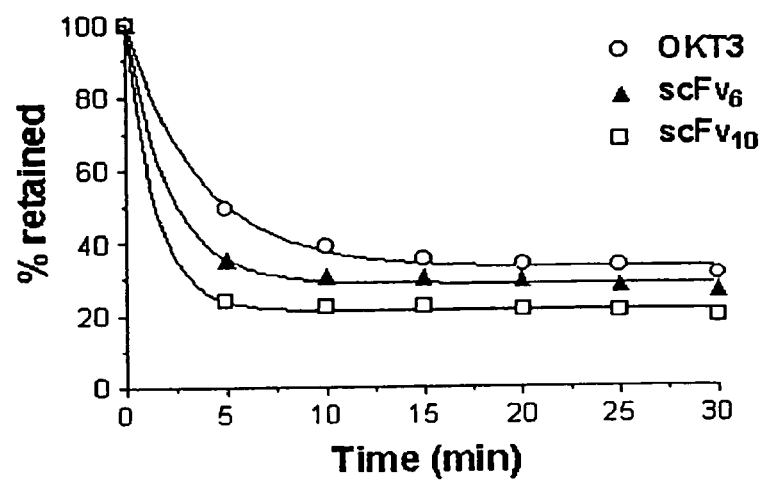

FIG. 7: Retention of anti-CD3 antibodies on the surface of CD3$^+$ Jurkat cells at 37° C.

Cell-surface retention of mAb OKT3 (circles), scFv$_6$ (triangles) and scFv$_{10}$ (squares) on CD3$^+$ Jurkat cells was measured. Values are expressed as a percentage of initial mean fluorescence intensity.

Figure 8:
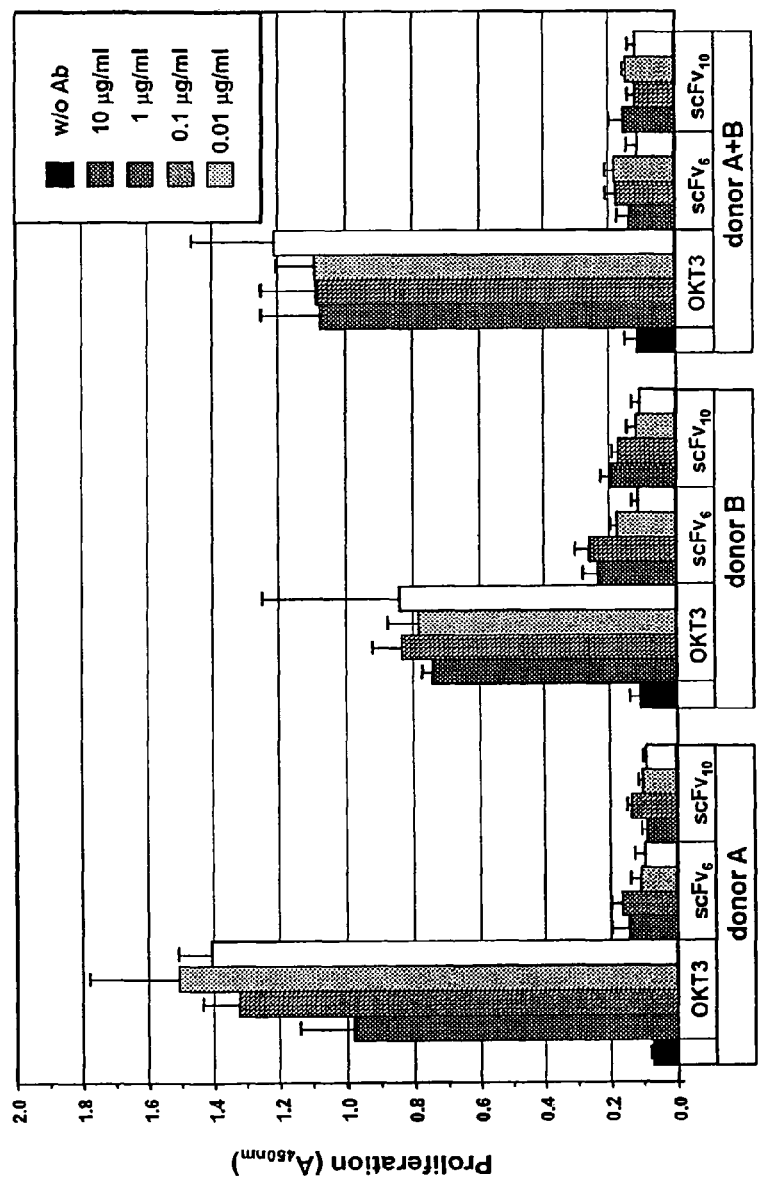

FIG. 8: Proliferation of peripheral blood mononuclear cells (PBMC) after 24 h incubation in presence of mAb OKT3 and anti-CD3 scFv-antibodies at concentrations of 0.01-10 μg/ml PBMCs from healthy donor A or donor B alone and mixed lymphocyte culture of PBMCs from donor A plus B were seeded in microtiter plates at density of 2×10$^5$ cells/well either without antibodies or in presence of serial dilutions of mAb OKT3, anti-CD3 scFv$_6$ and anti-CD3 scFv$_{10}$. After 24 h incubation, the cells were pulsed with 10 μM BrdU for 18 h. Incorporation of BrdU was determined by BrdU-ELISA. The means and SDs of triplicates are shown.

Figure 9:
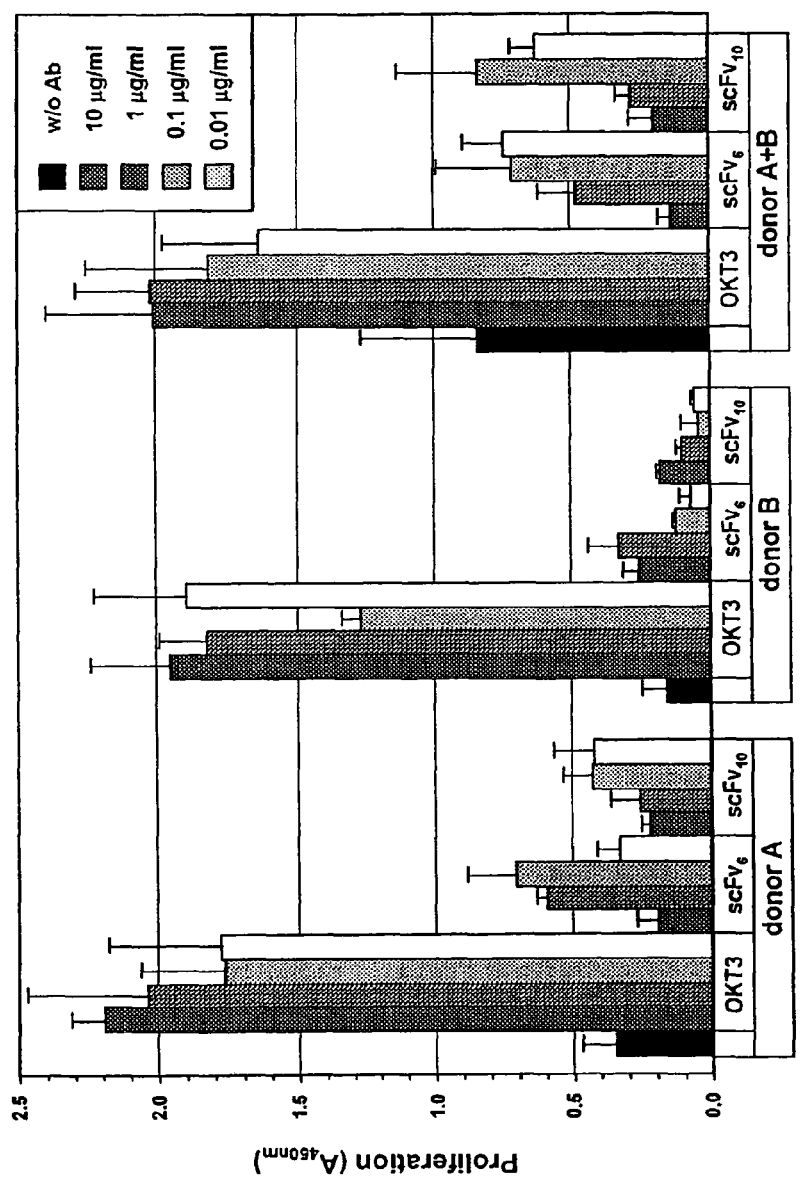

FIG. 9: Proliferation of PBMC after 72 h incubation in presence of mAb OKT3 and anti-CD3 scFv-antibodies at concentrations of 0.01-10 μg/ml PBMCs from healthy donor A or donor B alone and mixed lymphocyte culture of PBMCs from donor A plus B were seeded in microtiter plates at density of 2×10$^5$ cells/well either without antibodies or in presence of serial dilutions of mAb OKT3, anti-CD3 scFv$_6$ and anti-CD3 scFv$_{10}$. After 72 h incubation, the cells were pulsed with 10 μM BrdU for 18 h. Incorporation of BrdU was determined by BrdU-ELISA. The means and SDs of triplicates are shown.

Figure 10:
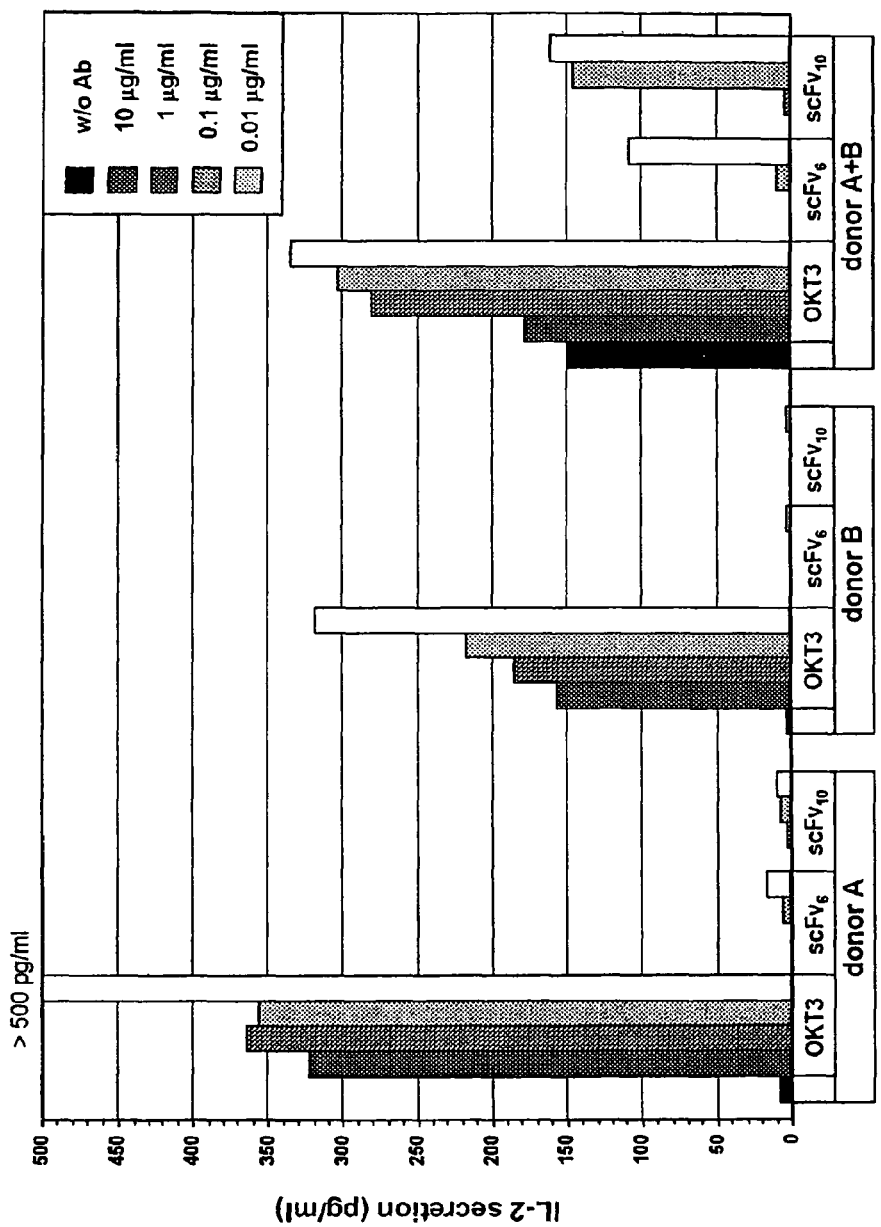

FIG. 10: Release of IL-2 by PBMCs after 24 h incubation in presence of mAb OKT3 and anti-CD3 scFv-antibodies at concentrations of 0.01-10 μg/ml PBMCs from healthy donor A or donor B alone and mixed lymphocyte culture of PBMCs from donor A plus B were seeded in 24-well plates at a density of 2×10$^6$ cells/well either without antibodies or in presence of serial dilutions of mAb OKT3, anti-CD3 scFv$_6$ and anti-CD3 scFv$_{10}$. After 24 h incubation, samples from the culture supernatants were harvested and the IL-2 concentration was measured by ELISA. The mean values of duplicates are shown.

Figure 11:
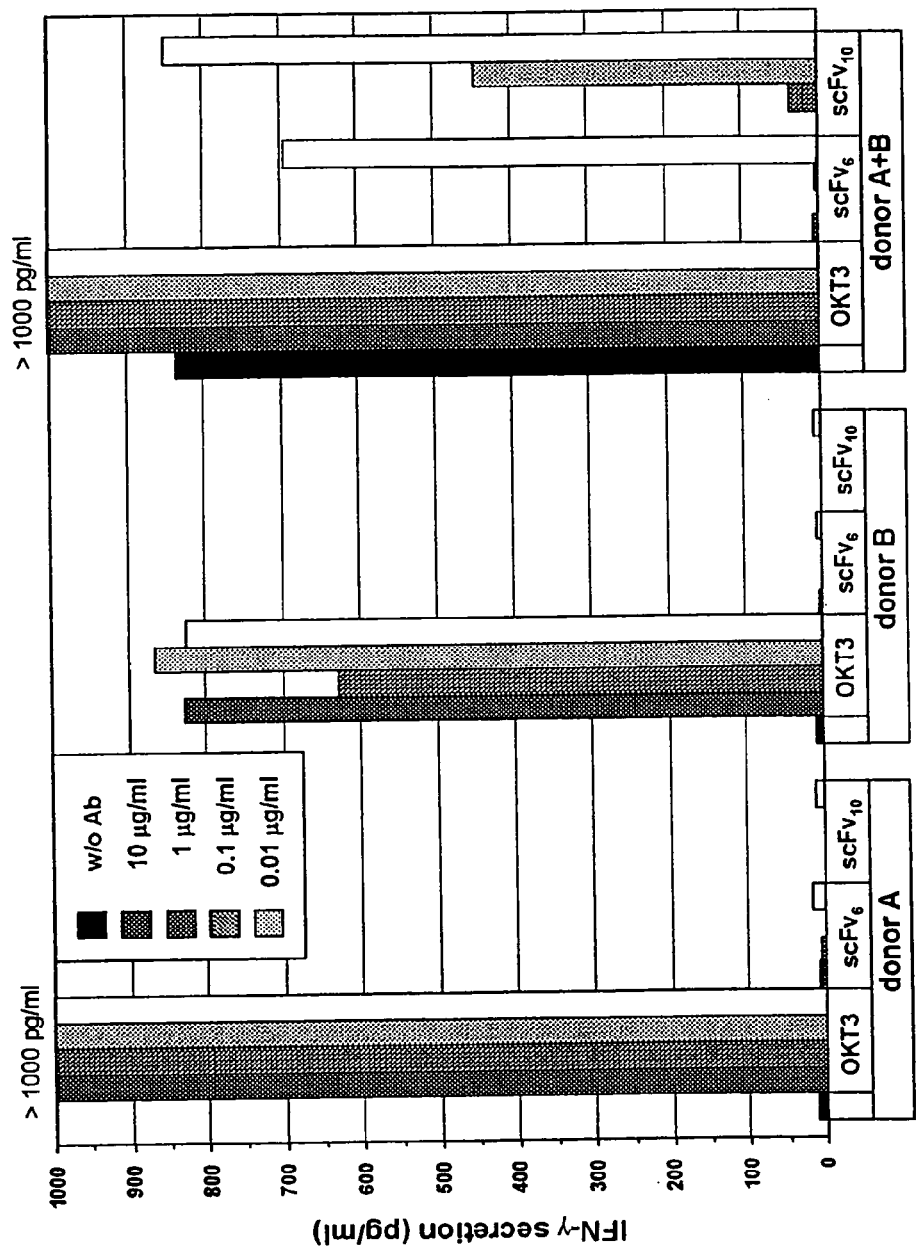

FIG. 11: Release of IFN-α by PBMCs after 72 h incubation in presence of mAb OKT3 and anti-CD3 scFv-antibodies at concentrations of 0.01-10 μg/ml PBMCs from healthy donor A or donor B alone and mixed lymphocyte culture of PBMCs from donor A plus B were seeded in 24-well plates at a density of 2×10$^6$ cells/well either without antibodies or in presence of serial dilutions of mAb OKT3, anti-CD3 scFv$_6$ and anti-CD3 scFv$_{10}$. After 72 h incubation, the samples of culture supernatants were harvested and the concentration of IFN-α was measured by ELISA. The mean values of duplicates are shown.

Figure 12:
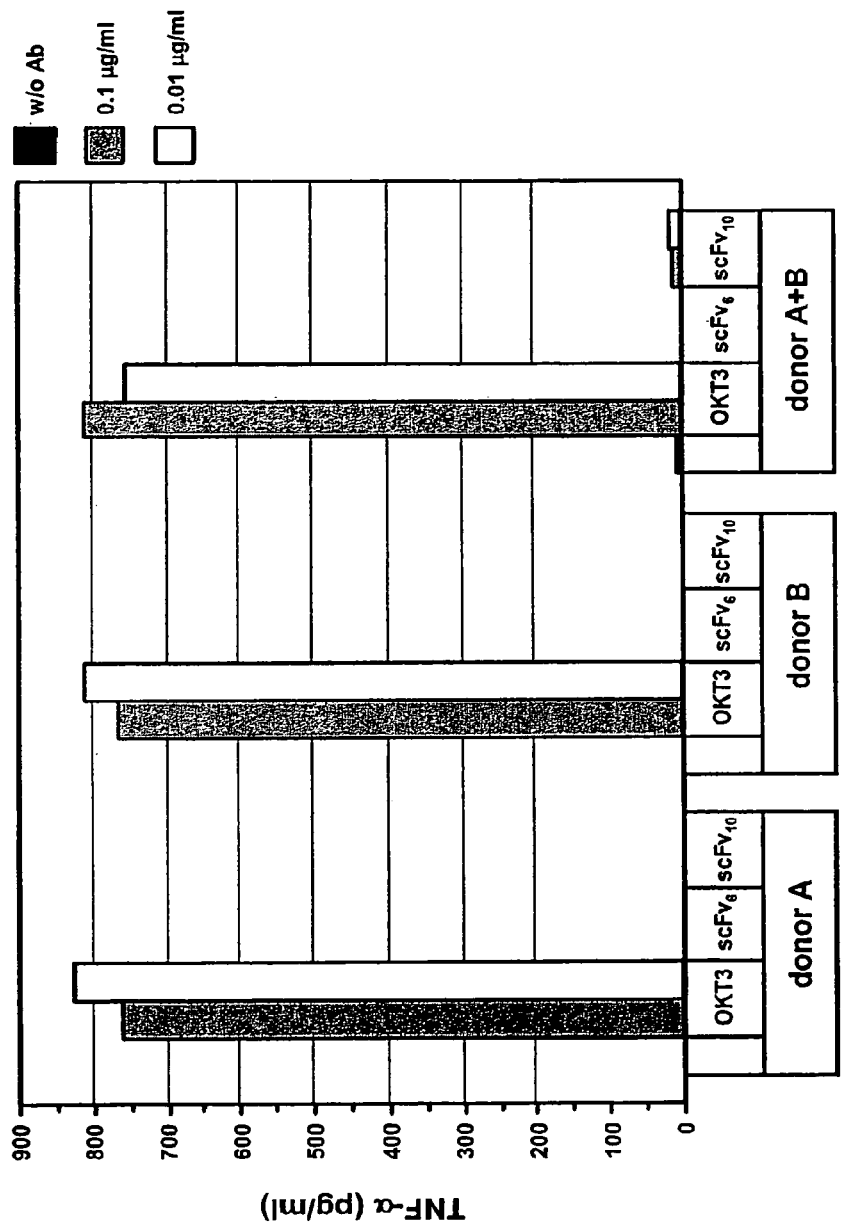

FIG. 12: Release of TNF-α by PBMCs after 36 h incubation in the presence of mAb OKT3 and anti-CD3 scFv-antibodies at concentrations of 0.01-0.1 μg/ml PBMCs from healthy donor A or donor B alone and mixed lymphocyte culture of PBMCs from donor A plus B were seeded in 24-well plates at a density of 2×10$^6$ cells/well either without antibodies or in presence 0.1 μg/ml and 0.01 μg/ml of mAb OKT3, anti-CD3 scFv$_6$ and anti-CD3 scFv$_{10}$. After 36 h incubation, samples of the culture supernatants were harvested and the concentration of TNF-α was measured by ELISA. The mean values of duplicates are shown.

Figure 13:
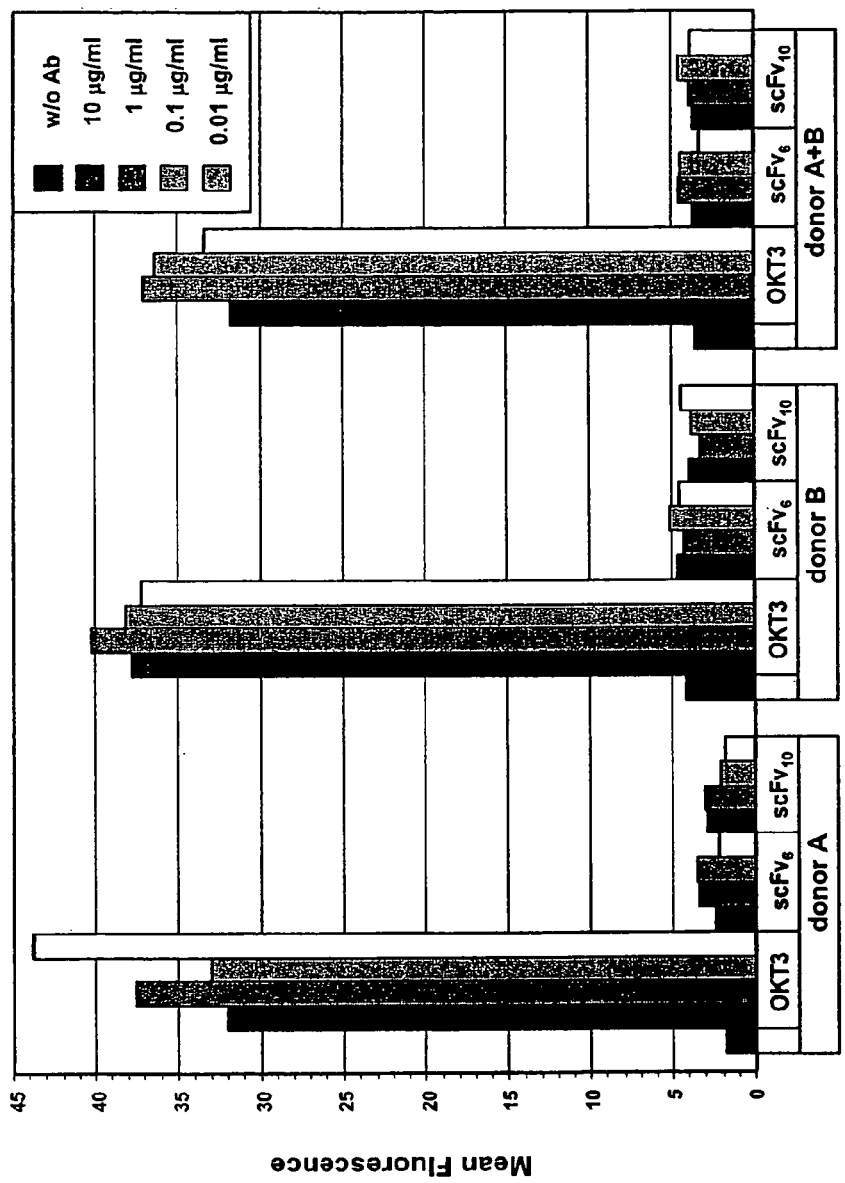

FIG. 13: Induction of the expression of IL-2Rα (CD25) on T cells after 90 h incubation of PBMC cultures in presence of mAb OKT3 and anti-CD3 scFv-antibodies at concentrations of 0.01-10 μg/ml PBMCs from healthy donor A or donor B alone and mixed lymphocyte culture of PBMCs from donor A plus B were seeded in 24-well plates at a density of 2×10$^6$ cells/well either without antibodies or in presence of serial dilutions of mAb OKT3, anti-CD3 scFv$_6$ and anti-CD3 scFv$_{10}$. After 90 h incubation, the CD25 expression was detected by flow cytometry using anti-CD25 mAb B1.49.9. Mean fluorescence intensity values after subtracting background fluorescence are shown.

Figure 14:
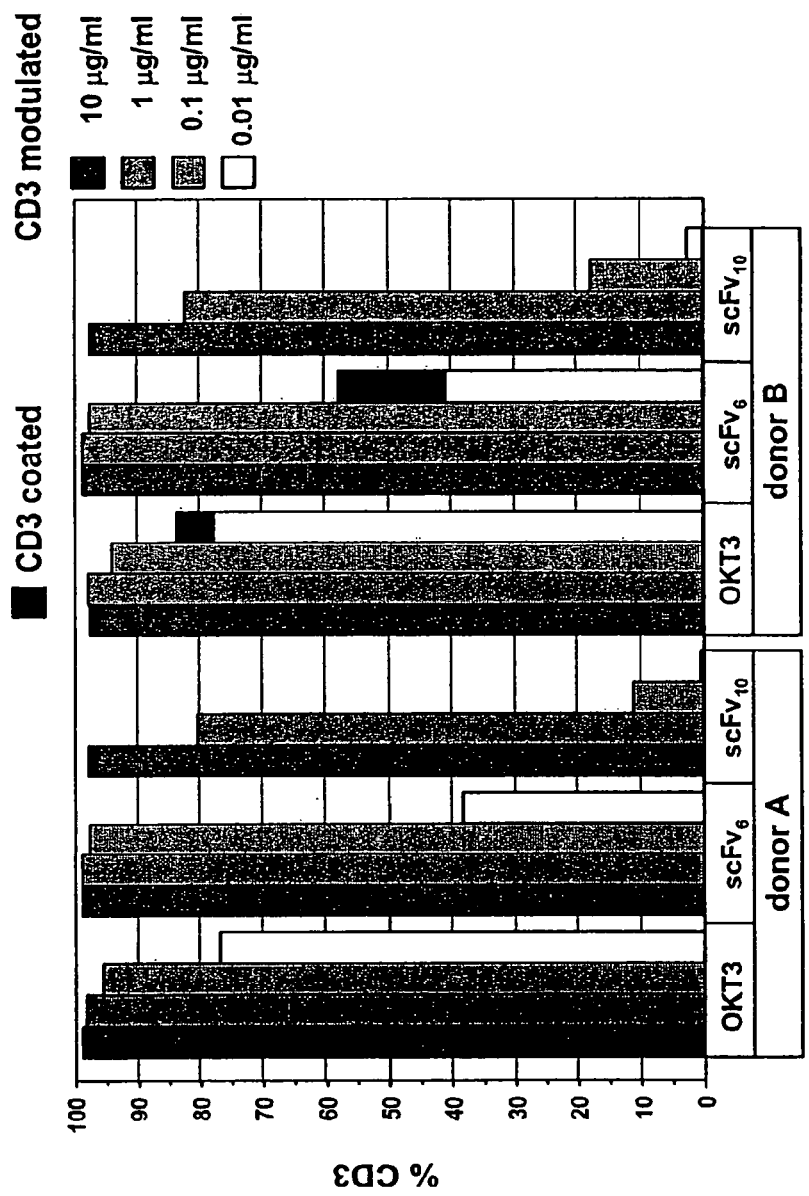

FIG. 14: CD3 modulation and coating by mAb OKT3 and anti-CD3 scFv-antibodies

PBMCs from healthy donor A or donor B were seeded in 24-well plates at a density of 2×10$^6$ cells/well either without antibodies or in presence of serial dilutions of mAb OKT3, anti-CD3 scFv$_6$ and anti-CD3 scFv$_{10}$. After 24 h incubation, the cells were harvested and stained with FITC-conjugated anti-CD3 mAb OKT3, PC5-conjugated anti-TCRα/β mAb BMA031. T cells were counterstained with anti-CD5 mAb and analyzed by flow cytometry. Data for CD3 modulation represent the percentage of TCR/CD3 complexes on the surface of treated CD5-positive T cells as a fraction of TCR/CD3 complexes on the surface of untreated CD5-positive T cells. CD3 coating is shown as the fraction of TCR/CD3 complexes which could not be detected by FITC-conjugated OKT3.

FIG. 15: (a) DNA sequence of plasmid pSKK3-scFv6_anti-CD3 (SEQ ID NO:16); (b) amino acid sequence of the $V_H$ and $V_L$ connected by the peptide linker SAKTTP encoded by the DNA sequence contained in pSKK3-scFv6_anti-CD3 (SEQ ID NO:17)

DETAILED DESCRIPTION OF THE INVENTION

Thus, the present invention relates to an antibody characterized by the following features:
(a) it is capable of suppressing an immune reaction;
(b) it is devoid of constant antibody regions; and
(c) it binds an epitope on the CD3 complex of the T-cell receptor.

The antibody of the present invention is specific to human TCR/CD3 complex present on all T cells regardless their MHC specificity. Such antibody is capable to suppress the activated T lymphocytes without any significant release of inflammatory cytokines, thus avoiding many of the unpleasant side-effects. The release of cytokines, e.g., IL-2, IFN γ and TNF-α is reduced by a factor more than 100 compared to OKT3. This is in sharp contrast with any known immunosuppressive antibodies. Although immunosuppression can be achieved by the administering such traditional antibodies to humans, their efficacy is often compromised by two factors: the first-dose syndrome resulting from T-cell activation, and the anti-globulin response (e.g. HAMA response) resulting from multiple injections of foreign proteins of non-human origin. The symptoms of antibody toxicity include fever, chills, diarrhea, and vomiting and in severe cases have resulted in death. The syndrome is caused by the release of inflammatory cytokines as result of transient T cell activation. Such activation depends on the interaction of the Fc portion of the antibody and Fc receptors (FcR) on accessory cells to cross-link the CD3 complexes on T cells. The Fc portion of mAbs of murine origin is also the main reason of anti-globulin response. The antibody of the present invention is devoid of the immunoglobulin constant domains and, therefore, is not able to interact with FcRs and is also much less immunogenic.

The antibodies of the present invention can be prepared by methods known to the person skilled in the art, e.g. by the following methods:

(a) Construction of single chain Fv-antibodies by combining the genes encoding at least two immunoglobulin variable $V_H$ and $V_L$ domains, either separated by peptide linkers or by no linkers, into a single genetic construct and expressing it in bacteria or other appropriate expression system.

(b) Non-covalent dimerization or multimerization of single chain Fv-antibodies comprising at least two $V_H$ and $V_L$ specific to human CD3 either separated by peptide linkers or by no linkers, in an orientation preventing their intramolecular pairing.

The term "capable of suppressing an immune reaction" means that the antibody is able, on the one hand, to prevent activation of T lymphocytes by foreign alloantigen and, on the other hand, to selectively deplete already activated T cells.

The antibody of the present invention may be a monovalent, bivalent or multivalent antibody.

Figure 1:
FIG. 1: Schematic representation of mono- and multivalent single chain Fv-antibody constructs Diabody: non-covalent scFv dimer; scDb: single chain diabody; scFv: single chain Fv fragment; (scFv)$_2$: scFv-scFv dimer. The antibody $V_H$ and $V_L$ domains are shown as black and gray ovals, respectively.
Figure 1:
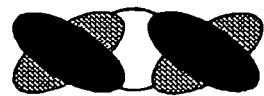
Figure 1:
Figure 1:
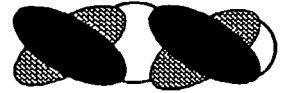

In a preferred embodiment, the antibody of the present invention is a non-covalent dimer of a single-chain Fv-antibody (scFv) ("diabody"; see FIG. 1) comprising CD3-specific $V_H$ and $V_L$ domains, either separated by peptide linkers or by no linkers.

In a further preferred embodiment, the antibody of the present invention comprises two single-chain Fv-antibodies (scFv) (see FIG. 1) comprising CD3-specific $V_H$ and $V_L$ domains.

In a further preferred embodiment, the antibody of the present invention is a single chain diabody (see FIG. 1) comprising CD3-specific $V_H$ and $V_L$ domains.

The term "Fv-antibody" as used herein relates to an antibody containing variable domains but not constant domains. The term "peptide linker" as used herein relates to any peptide capable of connecting two variable domains with its length depending on the kinds of variable domains to be connected. The peptide linker might contain any amino acid residue, although the amino acid combinations SAKTTP (SEQ ID NO:1) or SAKTTPKLGG (SEQ ID NO:2) are preferred. The peptide linker connecting single scFv of (scFv)$_2$ and single chain diabodies (scDb) might contain any amino acid residue, although one-to-three repeats of amino acid combination GGGGS (SEQ ID NO:3) are preferred for (scFv)$_2$ and three-to-four repeats of GGGGS (SEQ ID NO:3) are preferred for scDb.

In a more preferred embodiment, the antibody of the present invention contains variable domains substantially corresponding to the variable domains of the antibody produced by the hybridoma of ATCC deposit number CRL 8001.

In an even more preferred embodiment, the antibody of the present invention is characterized in that a cysteine at position H100A (Kabat numbering system) has been replaced by another amino acid, preferably by a serine.

The present invention also relates to a polynucleotide encoding an antibody of the present invention and vectors, preferably expression vectors containing said polynucleotides. The recombinant vectors can be constructed according to methods well known to the person skilled in the art; see, e.g., Sambrook, Molecular Cloning A Laboratory Manual, Cold Spring Harbor Laboratory (1989) N.Y.

A variety of expression vector/host systems may be utilized to contain and express sequences encoding the antibody of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector-enhancers, promoters, 5'- and 3'-untranslated regions which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding the multivalent multimeric antibody, vectors based on SV40 or EBV may be used with an appropriate selectable marker.

In bacterial systems, a number of expression vectors may be selected depending upon the use intended for the antibody of the present invention. Vectors suitable for use in the present invention include, but are not limited to the pSKK expression vector for expression in bacteria.

In the yeast, *Saccharomyces cerevisiae*, a number of vectors containing constitutive or inducible promoters such as alpha factor, alcohol oxidase, and PGH may be used; for reviews, see Grant et al. (1987) Methods Enzymol. 153:516-544.

In cases where plant expression vectors are used, the expression of sequences encoding the antibody of the present invnetion may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S. and Murry, L. E. in McGraw Hill Yearbook of Science and Technology (1992) McGraw Hill, New York, N.Y.; pp. 191-196.

An insect system may also be used to express the antibodies of the present invention. For example, in one such system, Autographa californica nuclear polyhedrosis virus (AcNPV)

is used as a vector to express foreign genes in *Spodoptera frugiperda* cells or in *Trichoplusia* larvae. The sequences encoding said antibodies may be cloned into a non-essential region of the virus, such as the polyhedrin gene, and placed under control of the polyhedrin promoter. Successful insertion of the gene encoding said antibody will render the polyhedrin gene inactive and produce recombinant virus lacking coat protein. The recombinant viruses may then be used to infect, for example, *S. frugiperda* cells or *Trichoplusia* larvae in which APOP may be expressed (Engelhard, E. K. et al. (1994) Proc. Nat. Acad. Sci. 91:3224-3227).

In mammalian host cells, a number of viral-based expression systems may be utilized. In cases where an adenovirus is used as an expression vector, sequences encoding an antibody of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the antibody in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding the antibody of the present invention. Such signals include the ATG initiation codon and adjacent sequences. In cases where sequences encoding the antibody, its initiation codon, and upstream sequences are inserted into the appropriate expression vector, no additional transcriptional or translational control signals may be needed. However, in case where only coding sequence is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed antibody chains in the desired fashion. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign antibody chains.

For long-term, high-yield production of recombinant antibodies, stable expression is preferred. For example, cell lines which stably express the antibody may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1980) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides neomycin and G-418 (Colbere-Garapin, F. et al (1981) J. Mol. Biol. 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047-51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

A particular preferred expression vector is pSKK3-scFv6_anti-CD3 deposited with the DSMZ (Deutsche Sammlung fur Mikroorganismen and Zellen) according to the Budapest Treaty under DSM 15137 on Aug. 16, 2002.

The present invention also relates to a composition containing an antibody, polynucleotide or an expression vector of the present invention. Preferably, said composition is a pharmaceutical composition preferably combined with a suitable pharmaceutical carrier. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

A preferred medical use of the compounds of the present invention described above is immunotherapy, preferably a therapy against acute transplant rejections and possibly against autoimmune diseases, such as type I diabetes, multiple sclerosis and rheumatoid arthritis.

The examples below explain the invention in more detail.

Example 1

Figure 2:
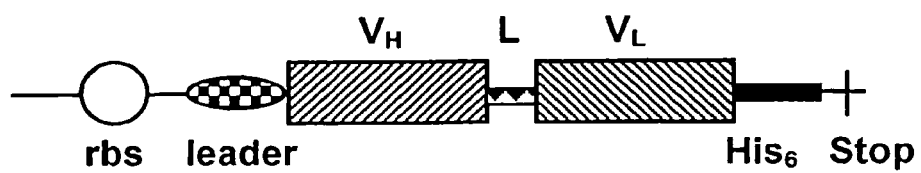
FIG. 2: Expression cassettes for anti-CD3 scFv constructs

Construction of the Plasmids pHOG-scFv10/Anti-CD3, pHOG-scFv6/Anti-CD3, pSKK3-scFv10/Anti-CD3 And pSKK3-scFv6/Anti-CD3 For the Expression of Anti-CD3 scFv$_{10}$ and scFv$_6$ Antibodies in Bacteria For constructing the genes encoding the anti-CD3 scFv$_{10}$ and scFv$_6$ (FIG. 2), the plasmid pHOG21-dmOKT3 containing the gene for anti-human CD3 scFv$_{18}$ (Kipriyanov et al., 1997, Protein Engineering 10, 445-453) was used. To facilitate the cloning procedures, NotI restriction site was introduced into the plasmid pHOG21-dmOKT3 by PCR amplification of scFv$_{18}$ gene using primers Bi3sk, 5'-CAGCCGGCCATGGCGCAGGTGCAACTGCAGCAG (SEQ ID NO:4) and Bi9sk, 5'-GAAGATGGATCCAGCGGCCGCAGTATCAGCCCGGTT (SEQ ID NO:5). The resulting 776 by PCR fragment was digested with NcoI and NotI and cloned into the NcoI/NotI-linearized vector pHOG21-CD19 (Kipriyanov et al., 1996, J. Immunol. Methods 196, 51-62), thus generating the plasmid pHOG21-dmOKT3+Not. The gene coding for OKT3 V$_H$ domain with a Cys-Ser substitution at position 100A according to Kabat numbering scheme (Kipriyanov et al., 1997, Protein Engineering 10, 445-453) was amplified by PCR with primers DP1, 5'-TCACACAGAATTCTTAGATCTATTAAAGAGGAGAAATTAACC (SEQ ID NO:6) and either DP2, 5'-AGCACACGATATCACCGCCAAGCTTGGGTGTTGTTTTGGC (SEQ ID NO:7) or OKT_5, 5'-TATTAAGATATCGGGTGTTGTTTTGGCTGAGGAG (SEQ ID NO:8), to generate the genes for V$_H$ followed by linkers of 10 and 6 amino acids, respectively (FIG. 2). The resulting 507 by and 494 by PCR fragments were digested with NcoI and EcoRV and cloned into NcoI/EcoRV-linearized plasmid pHOG21-dmOKT3+Not, thus generating the plasmids pHOG21-scFv10/anti-CD3 and pHOG21-scFv6/anti-CD3, respectively.

To increase the yield of functional scFv-antibodies in the bacterial periplasm, an optimized expression vector pSKK3 was generated (FIG. 3). This vector was constructed on the basis of plasmid pHKK (Horn et al., 1996, Appl. Microbiol. Biotechnol. 46, 524-532) containing hok/sok plasmid-free cell suicide system (Thisted et al., 1994, EMBO J. 13, 1960-1968). First, the gene coding for hybrid scFv V$_H$3-V$_L$19 was amplified by PCR from the plasmid pHOG3-19 (Kipriyanov et al., 1998, Int. J. Cancer 77, 763-772) using the primers 5-NDE, 5'-GATATACATATGAAATACCTATTGCCTACGGC (SEQ ID NO:9), and 3-AFL, 5'-CGAATTCTTAAGTTAGCACAGGCCTCTAGAGACACACAGATCTTTAG (SEQ ID NO:10). The resulting 921 by PCR fragment was digested with NdeI and AflII and cloned into the NdeI/AflII linearized plasmid pHKK generating the vector pHKK3-19. To delete an extra XbaI site, a fragment of pHKK plasmid containing 3'-terminal part of the lacI gene (encoding the lac repressor), the strong transcriptional terminator tHP and wild-type lac promoter/operator was amplified by PCR using primers 5-NAR, 5'-CACCCGGCGCCCAATACGCAAACCGCC (SEQ ID NO:11), and 3-NDE, 5'-GGTATTTCATATGTATATCTCCTTCTTCAGAAATTCGTAATCATGG (SEQ ID NO:12). The resulting 329 by DNA fragment was digested with NarI and NdeI and cloned into NarI/NdeI-linearized plasmid pHKK3-19 generating the vector pHKK☐Xba. To introduce a gene encoding the Skp/OmpH periplasmic factor for higher recombinant antibody production (Bothmann and Plückthun, 1998, Nat. Biotechnol. 16, 376-380), the skp gene was amplified by PCR with primers skp-3, 5'-CGAATTCTTAAGAAGGAGATATACATATGAAAAAGTGGTTATTAGCTGCAGG (SEQ ID NO:13) and skp-4, 5'-CGAATTCTCGAGCATTATTTAACCTGTTTCAGTACGTCGG (SEQ ID NO:14) using as a template the plasmid pGAH317 (Holck and Kleppe, 1988, Gene 67, 117-124). The resulting 528 by PCR fragment was digested with AflII and XhoI and cloned into the AflII/XhoI digested plasmid pHKK☐Xba resulting in the expression plasmid pSKK2. For removing the sequence encoding potentially immunogenic c-myc epitope, the NcoI/XbaI-linearized plasmid pSKK2 was used for cloning the NcoI/XbaI-digested 902 by PCR fragment encoding the scFv phOx31E (Marks et al., 1997, BioTechnology 10, 779-783), which was amplified with primers DP1 and His-Xba, 5'-CAGGCCTCTAGATTAGTGATGGTGATGGTGATGGG (SEQ ID NO:15). The resulting plasmid pSKK3 was digested with NcoI and NotI and used as a vector for cloning the genes coding for anti-CD3 scFv$_6$ and scFv$_{10}$, that were isolated as 715 by and 727 by DNA fragments after digestion of plasmids pHOG21-scFv6/anti-CD3 and pHOG21-scFv10/anti-CD3, respectively, with NcoI and NotI.

The generated plasmids pSKK3-scFv6/anti-CD3 (FIG. 3) and pSKK3-scFv10/anti-CD3 contain several features that improve plasmid performance and lead to increased accumulation of functional bivalent product in the *E. coli* periplasm under conditions of both shake-flask cultivation and high cell density fermentation. These are the hok/sok post-segregation killing system, which prevents plasmid loss, strong tandem ribosome-binding sites and a gene encoding the periplasmic factor Skp/OmpH that increases the functional yield of antibody fragments in bacteria. The expression cassette is under the transcriptional control of the wt lac promoter/operator system and includes a short sequence coding for the N-terminal peptide of β-galactosidase (lacZ') with a first rbs derived from the *E. coli* lacZ gene, followed by genes encoding the scFv-antibody and Skp/OmpH periplasmic factor under the translational control of strong rbs from gene 10 of phage T7 (T7g10). Besides, the gene of scFv-antibody is followed by a nucleotide sequence encoding six histidine residues for both immunodetection and purification of recombinant product by immobilized metal-affinity chromatography (IMAC).

Example 2

Production in Bacteria And Purification of scFv-Antibodies

The *E. coli* K12 strain RV308 (Δlacχ74 galISII:: OP308strA) (Maurer et al., 1980, J. Mol. Biol. 139, 147-161) (ATCC 31608) was used for functional expression of scFv-antibodies. The bacteria transformed with the expression plasmids pSKK3-scFv6/anti-CD3 and pSKK3-scFv10/anti-CD3, respectively, were grown overnight in 2xYT medium with 100 µg/ml ampicillin and 100 mM glucose (2xYT$_{GA}$) at 26° C. The overnight cultures were diluted in fresh 2xYT$_{GA}$ medium till optical density at 600 nm (OD$_{600}$) of 0.1 and continued to grow as flask cultures at 26° C. with vigorous shaking (180-220 rpm) until OD$_{600}$ reached 0.6-0.8. Bacteria were harvested by centrifugation at 5,000 g for 10 min at 20° C. and resuspended in the same volume of fresh YTBS medium (2xYT containing 1 M sorbitol, 2.5 mM glycine betaine and 50 µg/ml ampicillin). Isopropyl-β-D-thiogalactopyranoside (IPTG) was added to a final concentration of 0.2 mM and growth was continued at 21° C. for 14-16 h. Cells were harvested by centrifugation at 9,000 g for 20 min at 4° C. To isolate soluble periplasmic proteins, the pelleted bacteria were resuspended in 5% of the initial volume of ice-cold 200 mM Tris-HCl, 20% sucrose, 1 mM EDTA, pH 8.0. After 1 h incubation on ice with occasional stirring, the spheroplasts were centrifuged at 30,000 g for 30 min and 4° C. leaving the soluble periplasmic extract as the supernatant and spheroplasts plus the insoluble periplasmic material as the pellet. The periplasmic extract was thoroughly dialyzed against 50 mM Tris-HCl, 1 M NaCl, pH 7.0, and used as a starting material for isolating scFv-antibodies. The recombinant product was concentrated by ammonium sulfate precipitation (final concentration 70% of saturation). The protein precipitate was collected by centrifugation (10,000 g, 4° C., 40 min) and dissolved in 10% of the initial volume of 50 mM Tris-HCl, 1 M NaCl, pH 7.0, followed by thorough dialysis against the same buffer. Immobilized metal affinity chromatography (IMAC) was performed at 4° C. using a 5 ml column of Chelating Sepharose (Amersham Pharmacia, Freiburg, Germany) charged with $Cu^{2+}$ and equilibrated with 50 mM Tris-HCl, 1 M NaCl, pH 7.0 (start buffer). The sample was loaded by passing the sample over the column by gravity flow. The column was then washed with twenty column volumes of start buffer followed by start buffer containing 50 mM imidazole until the absorbance (280 nm) of the effluent was minimal (about thirty column volumes). Absorbed material was eluted with 50 mM Tris-HCl, 1 M NaCl, 300 mM imidazole, pH 7.0, as 1 ml fractions. The eluted fractions containing recombinant protein were identified by reducing 12% SDS-PAGE followed by Coomassie staining. The positive fractions were pooled and subjected to buffer exchange for 50 mM imidazole-HCl, 50 mM NaCl (pH 7.0) using pre-packed PD-10 columns (Pharmacia Biotech, Freiburg, Germany). The turbidity of protein solution was removed by centrifugation (30,000 g, 1 h, 4° C.).

The final purification was achieved by ion-exchange chromatography on a Mono S HR 5/5 column (Amersham Pharmacia, Freiburg, Germany) in 50 mM imidazole-HCl, 50 mM NaCl, pH 7.0, with a linear 0.05-1 M NaCl gradient. The fractions containing scFv-antibody were concentrated with simultaneous buffer exchange for PBS containing 50 mM imidazole, pH 7.0 (PBSI buffer), using Ultrafree-15 centrifugal filter device (Millipore, Eschborn, Germany). Protein concentrations were determined by the Bradford dye-binding assay (Bradford, 1976, Anal. Biochem., 72, 248-254) using the Bio-Rad (Munich, Germany) protein assay kit. SDS-PAGE analysis demonstrated that anti-CD3 $scFv_{10}$ and $scFv_6$ migrated as single bands with a molecular mass ($M_r$) around 30 kDa (FIG. 4). Size-exclusion chromatography on a calibrated Superdex 200 HR 10/30 column (Amersham Pharmacia) demonstrated that $scFv_6$ was mainly in a dimeric form with $M_r$ around 60 kDa, while $scFv_{10}$ was pure monomer (FIG. 5).

Example 3

Cell Binding Measurements

The human $CD3^+$ T-cell leukemia cell line Jurkat was used for flow cytometry experiments. The cells were cultured in RPMI 1640 medium supplemented with 10% heat-inactivated fetal calf serum (FCS), 2 mM L-glutamine, 100 U/mL penicillin G sodium and 100 μg/ml streptomycin sulfate (all from Invitrogen, Groningen, The Netherlands) at 37° C. in a humidified atmosphere with 5% $CO_2$. $1 \times 10^6$ cells were incubated with 0.1 ml phosphate buffered saline (PBS, Invitrogen, Groningen, The Netherlands) supplemented with 2% heat-inactivated fetal calf serum (FCS, Invitrogen, Groningen, The Netherlands) and 0.1% sodium azide (Roth, Karlsruhe, Germany) (referred to as FACS buffer) containing diluted scFv-antibodies or mAb OKT3 (Orthoclone OKT3, Cilag, Sulzbach, Germany) for 45 min on ice. After washing with FACS buffer, the cells were incubated with 0.1 ml of 0.01 mg/ml anti-$(His)_6$ mouse mAb 13/45/31-2 (Dianova, Hamburg, Germany) in the same buffer for 45 min on ice. After a second washing cycle, the cells were incubated with 0.1 ml of 0.015 mg/ml FITC-conjugated goat anti-mouse IgG (Dianova, Hamburg, Germany) under the same conditions as before. The cells were then washed again and resuspended in 0.5 ml of FACS buffer containing 2 μg/ml propidium iodide (Sigma-Aldrich, Taufkirchen, Germany) to exclude dead cells. The fluorescence of $1 \times 10^4$ stained cells was measured using a Beckman-Coulter Epics XL flow cytometer (Beckman-Coulter, Krefeld, Germany). Mean fluorescence (F) was calculated using System-II and Expo32 software (Beckman-Coulter, Krefeld, Germany) and the background fluorescence was subtracted. Equilibrium dissociation constants ($K_d$) were determined by fitting the experimental values to the Lineweaver-Burk equation: $1/F = 1/F_{max} + (K_d/F_{max})(1/[Ab])$ using the software program PRISM (GraphPad Software, San Diego, Calif.).

The flow cytometry experiments demonstrated a specific interaction of scFv-antibodies to Jurkat cells expressing CD3 on their surface. The fluorescence intensities obtained for $scFv_6$ were significantly higher than for $scFv_{10}$ reflecting the 10-fold difference in affinity values for these two scFv-antibodies (FIG. 6, Table 1). The deduced affinity value for $scFv_6$ was fairly close to that of mAb OKT3 thus confirming the bivalent binding of $scFv_6$ to the cell surface.

Example 4

In Vitro Cell Surface Retention

To investigate the biological relevance of the differences between $scFv_6$, $scFv_{10}$ and OKT3 in direct binding experiments, the in vitro retention of the scFv-antibodies on the surface of $CD3^+$ Jurkat cells was determined by flow cytometry (FIG. 7). Cell surface retention assays were performed at 37° C. under conditions preventing internalization of cell surface antigens, as described (Adams et al., 1998, Cancer Res. 58, 485-490), except that the detection of retained scFv-antibodies was performed using mouse anti-$(His)_6$ mAb 13/45/31-2 (0.01 mg/ml; Dianova, Hamburg, Germany) followed by FITC-conjugated goat anti-mouse IgG (0.015 mg/ml; Dianova, Hamburg, Germany). Kinetic dissociation constant ($k_{off}$) and half-life ($t_{1/2}$) values for dissociation of antibodies were deduced from a one-phase exponential decay fit of experimental data using the software program PRISM (GraphPad Software, San Diego, Calif.). The monovalent $scFv_{10}$ had a relatively short retention half-life (1.02 min), while $scFv_6$ and OKT3 had 1.5-fold and 2.5-fold longer $t_{1/2}$, respectively, thus correlating well with their higher binding affinities deduced from the direct binding experiments (FIG. 7, Table 1).

TABLE 1

Affinity and kinetics of anti-CD3 antibodies binding to CD3$^+$ Jurkat cells

| Antibody | $K_d$ (nM) | $k_{off}$ (s$^{-1}$/10$^{-3}$) | $t_{1/2}$ (min) |
|---|---|---|---|
| mAb OKT3 | 2.06 | 4.47 | 2.59 |
| scFv$_6$ | 4.58 | 7.82 | 1.48 |
| scFv$_{10}$ | 51.92 | 11.33 | 1.02 |

The dissociation constants ($K_d$) were deduced from Lineweaver-Burk plots shown in FIG. 6. The $k_{off}$ values were deduced from Jurkat cell surface retention experiments shown in FIG. 7. The half-life values ($t_{1/2}$) for dissociation of antibody-antigen complexes were deduced from the ratio ln2/$k_{off}$.

Example 5

Isolation of Peripheral Blood Mononuclear Cells (PBMCs)

Human PBMCs were isolated from the heparinized peripheral blood of healthy volunteers by density gradient centrifugation. The blood samples were twice diluted with PBS (Invitrogen, Groningen, The Netherlands), layered on a cushion of Histopaque-1077 (Sigma-Aldrich, Taufkirchen, Germany) and centrifuged at 800 g for 25 min. The PBMCs located in the interface were collected and washed three times with PBS before use.

Example 6

Cell Proliferation Assay

Isolated PBMCs were resuspended in RPMI 1640 medium supplemented with 10% heat-inactivated FCS, 2 mM L-glutamine, 100 U/ml penicillin G sodium salt and 0.1 mg/ml streptomycin sulfate (all from Invitrogen, Groningen, The Netherlands) and placed to 96-well flat-bottom tissue culture plates (Greiner, Frickenhausen, Germany) at a density of 2×10$^5$ cells per well. Triplicates of cultures were incubated with serial dilutions of soluble antibodies at 37° C. in a humidified atmosphere containing 5% CO$_2$ for the indicated time followed by 18 h pulsing with 0.01 mM 5-bromo-2'-deoxyuridine (BrdU). Incorporation of BrdU was determined by Cell Proliferation ELISA (Roche, Mannheim, Germany) according to the manufacturers instructions.

During incubation for 24-36 h, neither scFv$_6$ nor scFv$_{10}$ induced proliferation of both autologous (donor A alone and donor B alone, respectively) and mixed lymphocyte cultures (donor A+B). In contrast, mAb OKT3 demonstrated high mitogenic activity for all tested 24 h cultures, obviously due to CD3-crosslinking via FcγR-bearing cells (FIG. 8).

The OKT3-induced T-cell proliferation was significantly higher in autologous PBMC cultures incubated for 72-90 h, while scFv$_6$ and scFv$_{10}$ demonstrated only minor effects in comparison with 24-h incubation (FIG. 9). In mixed PBMC cultures (donor A+B) incubated for 72 h without antibody treatment, a mixed lymphocyte reaction (MLR) developed. Treatment of mixed PBMC cultures with OKT3 had no effect on MLR, while both scFv-antibodies were able to suppress MLR in a concentration-dependent manner, thus reaching the background level at a concentration of 10 µg/ml (FIG. 9).

Example 7

Analyses of Cytokine Release

For measurement of cytokine secretion by activated lymphocytes, 2×10$^6$ PBMCs were plated in individual wells of 24-well plates (Greiner, Frickenhausen, Germany) in RPMI 1640 medium supplemented with 10% heat-inactivated FCS, 2 mM L-glutamine, 100 U/ml penicillin G sodium salt and 0.1 mg/ml streptomycin sulfate (all from Invitrogen, Groningen, The Netherlands) together with the indicated antibodies. For determination of secretion of IL-2, TNF-α and IFN-γ, aliquots of the culture supernatants were collected after 24 h, 36 h and 72 h, respectively. Cytokine levels were measured in duplicates using the commercially available ELISA kits for IL-2 (Pharmingen, San Diego, Calif.), TNF-α and IFN-γ (Endogen, Cambridge, Mass.).

In both autologous and mixed PBMC cultures, OKT3 induced a strong release of IL-2 (FIG. 10), IFN-γ (FIG. 11) and TNF-α (FIG. 12). In contrast, the autologous PBMC cultures treated with scFv$_6$ and scFv$_{10}$, respectively, did not produce IL-2 (FIG. 10), IFN-γ (FIG. 11) and TNF-α (FIG. 12). Mixed lymphocyte cultures incubated without antibodies demonstrated release of significant amounts of cytokines as a result of allogeneic stimulation. This secretion of IL-2 and IFN-γ could be suppressed by scFv-antibodies in a dose-dependent manner (FIGS. 10 and 11). Bivalent scFv$_6$ demonstrated approximately tenfold higher efficacy than scFv$_{10}$. In contrast, mAb OKT3 had rather induction than suppression of cytokine release in mixed PBMC cultures.

Example 8

Alteration of Surface Antigens on PBMCs Treated With Anti-CD3 Antibodies

For determination the cell surface expression of the alpha subunit of IL-2 receptor (CD25) as an early activation marker, 2×10$^6$ PBMCs were plated in individual wells of 24-well plates (Greiner, Frickenhausen, Germany) in RPMI 1640 medium supplemented with 10% heat-inactivated FCS, 2 mM L-glutamine, 100 U/ml penicillin-G sodium salt and 0.1 mg/ml streptomycin sulfate (all from Invitrogen, Groningen, The Netherlands) together with the indicated antibodies. The cells were harvested after 90 h incubation and stained for flow cytometric analysis with PE-conjugated anti-CD25 mAb B1.49.9 and with the corresponding isotype controls (all from Beckman-Coulter, Krefeld, Germany), as described in Example 3. 10$^4$ lymphocytes were analyzed with a Beckman-Coulter Epics XL flow cytometer (Beckman-Coulter, Krefeld, Germany). Mean fluorescence (F) was calculated using System-II software (Beckman-Coulter, Krefeld, Germany), and background fluorescence was subtracted.

PBMCs that were cultured in the presence of OKT3 showed a strong upregulation of the early activation marker IL-2R□ (CD25) on their surface, as determined by flow cytometry (FIG. 12). In contrast, none of the PBMC cultures treated either with scFv$_6$ or scFv$_{10}$ showed elevated levels of CD25 expression (FIG. 13). Thus, these results clearly demonstrate that, unlike mAb OKT3, scFv$_6$ and scFv$_{10}$ do not posses the T-cell activating properties.

Example 9

Modulation And Coating of TCR/CD3 On Lymphocytes Treated With Anti-CD3 Antibodies To measure the modulation and coating of cell surface TCR/CD3 on lymphocytes, $2 \times 10^6$ PBMCs were plated in individual wells of 24-well plates (Greiner, Frickenhausen, Germany) in RPMI 1640 medium supplemented with 10% heat-inactivated FCS, 2 mM L-glutamine, 100 U/ml penicillin-G sodium salt and 0.1 mg/ml streptomycin sulfate (all from Invitrogen, Groningen, The Netherlands) together with the indicated antibodies. The cells were harvested after 24 h incubation and stained for flow cytometric analysis with FITC-conjugated OKT3 (Dr. Moldenhauer, German Cancer Research Center, Heidelberg) or PC5-conjugated anti-TCRα/β (Beckman-Coulter, Krefeld, Germany) and the corresponding isotype controls (Beckman-Coulter, Krefeld, Germany). The cells were counterstained with anti-CD5 antibodies (Beckman-Coulter, Krefeld, Germany) for lymphocytes and analyzed with a Beckman-Coulter Epics XL flow cytometer (Beckman-Coulter, Krefeld, Germany). Mean fluorescence (F) of OKT3-FITC and TCR-PC5 from CD5-positive cells was calculated using System-II software (Beckman-Coulter, Krefeld, Germany). Calculation of CD3 modulation and coating was performed as described previously (Cole, M. S. et al., 1997, J. Immunol. 159, 3613-3621):

$$\% \ CD3 \ \text{modulation} = \frac{\text{untreated cells } F(\text{anti-}TCR) - \text{treated cells } F(\text{anti-}TCR)}{\text{untreated cells } F(\text{anti-}TCR)} \times 100$$

$$\% \ CD3 \ \text{coating} = \left[ \frac{\text{treated cells } F(\text{anti-}TCR)}{\text{control cells } F(\text{anti-}TCR)} - \frac{\text{treated cells } F(OKT3)}{\text{control cells}(OKT3)} \right] \times 100$$

Coating, which is defined as the number of CD3 molecules on the surface of T lymphocytes that are antibody bound and therefore not detectable by FITC-conjugated mAb OKT3, was only observed in one experiment with the lowest concentration of OKT3 and anti-CD3 $\text{scFv}_6$ (FIG. 14). CD3 modulation, which represents the fraction of TCR/CD3 complexes on the surface of T cells that is lost after antibody treatment, is efficiently (>90%) induced by mAb OKT3 and anti-CD3 $\text{scFv}_6$ at concentrations in the range between 0.1 µg/ml and 10 µg/ml (FIG. 14). In contrast, the modulation activity of anti-CD3 $\text{scFv}_{10}$ was much lower and could be observed only at concentrations above 1 µg/ml (FIG. 14).

---

SEQUENCE LISTING

<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: Peptide linker

<400> SEQUENCE: 1

Ser Ala Lys Thr Thr Pro
1               5

<210> SEQ ID NO 2
<211> LENGTH: 10
<212> TYPE: PRT
<213> ORGANISM: Artificial Sequence
<220> FEATURE:
<223> OTHER INFORMATION: Peptide linker

<400> SEQUENCE: 2

Ser Ala Lys Thr Thr Pro Lys Leu Gly Gly
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Peptide linker

<400> SEQUENCE: 3

Gly Gly Gly Gly Ser
1               5

<210> SEQ ID NO 4
<211> LENGTH: 33
<212> TYPE: DNA
<213> ORGANISM: Artificial Sequence

```
<220> FEATURE:
<223> OTHER INFORMATION: Primer Bi3sk

<400> SEQUENCE: 4
cagccggcca tggcgcaggt gcaactgcag cag                                    33

<210> SEQ ID NO 5
<211> LENGTH: 36
<212> TYPE: DNA
<213> ORGANISM: Artificial Sequence
<220> FEATURE:
<223> OTHER INFORMATION: Primer Bi9sk

<400> SEQUENCE: 5
gaagatggat ccagcggccg cagtatcagc ccggtt                                 36

<210> SEQ ID NO 6
<211> LENGTH: 42
<212> TYPE: DNA
<213> ORGANISM: Artificial Sequence
<220> FEATURE:
<223> OTHER INFORMATION: Primer DP1

<400> SEQUENCE: 6
tcacacagaa ttcttagatc tattaaagag gagaaattaa cc                          42

<210> SEQ ID NO 7
<211> LENGTH: 40
<212> TYPE: DNA
<213> ORGANISM: Artificial Sequence
<220> FEATURE:
<223> OTHER INFORMATION: Primer DP2

<400> SEQUENCE: 7
agcacacgat atcaccgcca agcttgggtg ttgttttggc                             40

<210> SEQ ID NO 8
<211> LENGTH: 34
<212> TYPE: DNA
<213> ORGANISM: Artificial Sequence
<220> FEATURE:
<223> OTHER INFORMATION: Primer OKT_5

<400> SEQUENCE: 8
tattaagata tcgggtgttg ttttggctga ggag                                   34

<210> SEQ ID NO 9
<211> LENGTH: 32
<212> TYPE: DNA
<213> ORGANISM: Artificial Sequence
<220> FEATURE:
<223> OTHER INFORMATION: Primer 5-NDE

<400> SEQUENCE: 9
gatatacata tgaaatacct attgcctacg gc                                     32

<210> SEQ ID NO 10
<211> LENGTH: 47
<212> TYPE: DNA
<213> ORGANISM: Artificial Sequence
<220> FEATURE:
<223> OTHER INFORMATION: Primer 3-AFL

<400> SEQUENCE: 10
cgaattctta agttagcaca ggcctctaga gacacacaga tctttag                     47
```

-continued

<210> SEQ ID NO 11
<211> LENGTH: 28
<212> TYPE: DNA
<213> ORGANISM: Artificial Sequence
<220> FEATURE:
<223> OTHER INFORMATION: Primer 5-NAR

<400> SEQUENCE: 11
caccctggcg cccaatacgc aaaccgcc                                      28

<210> SEQ ID NO 12
<211> LENGTH: 46
<212> TYPE: DNA
<213> ORGANISM: Artificial Sequence
<220> FEATURE:
<223> OTHER INFORMATION: Primer 3-NDE

<400> SEQUENCE: 12
ggtatttcat atgtatatct ccttcttcag aaattcgtaa tcatgg                  46

<210> SEQ ID NO 13
<211> LENGTH: 52
<212> TYPE: DNA
<213> ORGANISM: Artificial Sequence
<220> FEATURE:
<223> OTHER INFORMATION: Primer skp-3

<400> SEQUENCE: 13
cgaattctta agaaggagat atacatatga aaaagtggtt attagctgca gg           52

<210> SEQ ID NO 14
<211> LENGTH: 40
<212> TYPE: DNA
<213> ORGANISM: Artificial Sequence
<220> FEATURE:
<223> OTHER INFORMATION: Primer skp-4

<400> SEQUENCE: 14
cgaattctcg agcattattt aacctgtttc agtacgtcgg                         40

<210> SEQ ID NO 15
<211> LENGTH: 35
<212> TYPE: DNA
<213> ORGANISM: Artificial Sequence
<220> FEATURE:
<223> OTHER INFORMATION: Primer His-Xba

<400> SEQUENCE: 15
caggcctcta gattagtgat ggtgatggtg atggg                              35

<210> SEQ ID NO 16
<211> LENGTH: 6083
<212> TYPE: DNA
<213> ORGANISM: Artificial Sequence
<220> FEATURE:
<223> OTHER INFORMATION: Plasmid pSKK3-scFv6 anti-CD3

<400> SEQUENCE: 16
acccgacacc atcgaatggc gcaaaacctt tcgcggtatg gcatgatagc gcccggaaga    60
gagtcaattc agggtggtga atgtgaaacc agtaacgtta tacgatgtcg cagagtatgc   120
cggtgtctct tatcagaccg tttcccgcgt ggtgaaccag gccagccacg tttctgcgaa   180
aacgcgggaa aaagtggaag cggcgatggc ggagctgaat tacattccca accgggtggc   240
acaacaactg gcgggcaaac agtcgttgct gattggcgtt gccacctcca gtctggccct   300

```
gcacgcgccg tcgcaaattg tcgcggcgat taaatctcgc gccgatcaac tgggtgccag    360
cgtggtggtg tcgatggtag aacgaagcgg cgtcgaagcc tgtaaagcgg cggtgcacaa    420
tcttctcgcg caacgcgtca gtgggctgat cattaactat ccgctggatg accaggatgc    480
cattgctgtg gaagctgcct gcactaatgt tccggcgtta tttcttgatg tctctgacca    540
gacacccatc aacagtatta ttttctccca tgaagacggt acgcgactgg gcgtggagca    600
tctggtcgca ttgggtcacc agcaaatcgc gctgttagcg ggcccattaa gttctgtctc    660
ggcgcgtctg cgtctggctg gctggcataa atatctcact cgcaatcaaa ttcagccgat    720
agcggaacgg gaaggcgact ggagtgccat gtccggtttt caacaaacca tgcaaatgct    780
gaatgagggc atcgttccca ctgcgatgct ggttgccaac gatcagatgg cgctgggcgc    840
aatgcgcgcc attaccgagt ccgggctgcg cgttggtgcg gatatctcgg tagtgggata    900
cgacgatacc gaagacagct catgttatat cccgccgtta accaccatca acaggatttt    960
tcgcctgctg gggcaaacca gcgtggaccc ttgctgcaa ctctctcagg gccaggcggt    1020
gaagggcaat cagctgttgc ccgtctcact ggtgaaaaga aaaaccaccc tggcgcccaa    1080
tacgcaaacc gcctctcccc gcgcgttggc cgattcatta atgcagctgg cacgacaggt    1140
ttcccgactg gaaagcgggc agtgagcggt acccgataaa agcggcttcc tgacaggagg    1200
ccgttttgtt ttgcagccca cctcaacgca attaatgtga gttagctcac tcattaggca    1260
ccccaggctt tacactttat gcttccggct cgtatgttgt gtggaattgt gagcggataa    1320
caatttcaca caggaaacag ctatgaccat gattacgaat ttctgaagaa ggagatatac    1380
atatgaaata cctattgcct acggcagccg ctggcttgct gctgctggca gctcagccgg    1440
ccatggcgca ggtgcagctg cagcagtctg gggctgaact ggcaagacct ggggcctcag    1500
tgaagatgtc ctgcaaggct tctggctaca cctttactag gtacacgatg cactgggtaa    1560
aacagaggcc tggacaggt ctggaatgga ttggatacat taatcctagc cgtggttata    1620
ctaattacaa tcagaagttc aaggacaagg ccacattgac tacagacaaa tcctccagca    1680
cagcctacat gcaactgagc agcctgacat ctgaggactc tgcagtctat tactgtgcaa    1740
gatattatga tgatcattac agccttgact actggggcca aggcaccact ctcacagtct    1800
cctcagccaa acaacacccc gatatcgtgc tcactcagtc tccagcaatc atgtctgcat    1860
ctccagggga aaaggtcacc atgacctgca gtgccagctc aagtgtaagt tacatgaact    1920
ggtaccagca gaagtcaggc acctccccca aagatggat ttatgacaca tccaaactgg    1980
cttctggagt ccctgctcac ttcaggggca gtgggtctgg gacctcttac tctctcacaa    2040
tcagcggcat ggaggctgaa gatgctgcca cttattactg ccagcagtgg agtagtaacc    2100
cattcacgtt cggctcgggg acaaagttgg aaataaaccg ggctgatact gcggccgctg    2160
gatcccatca ccatcaccat cactaatcta gaggcctgtg ctaacttaag aaggagatat    2220
acatatgaaa aagtggttat tagctgcagg tctcggttta gcactggcaa cttctgctca    2280
ggcggctgac aaaattgcaa tcgtcaacat gggcagcctg ttccagcagg tagcgcagaa    2340
aaccggtgtt tctaacacgc tggaaaatga gttcaaaggc cgtgccagcg aactgcagcg    2400
tatggaaacc gatctgcagg ctaaaatgaa aaagctgcag tccatgaaag cgggcagcga    2460
tcgcactaag ctggaaaaag acgtgatggc tcagcgccag acttttgctc agaaagcgca    2520
ggcttttgag caggatcgcg cacgtcgttc caacgaagaa cgcggcaaac tggttactcg    2580
tatccagact gctgtgaaac ccgttgccaa cagccaggat atcgatctgg ttgttgatgc    2640
```

```
aaacgccgtt gcttacaaca gcagcgatgt aaaagacatc actgtcgacg tactgaaaca      2700
ggttaaataa tgctcgagga actgctgaaa catctgaagg agctgcttaa aggtgagttc      2760
tgataagctt gacctgtgaa gtgaaaaatg gcgcacattg tgcgacattt tttttgtctg      2820
ccgtttaccg ctactgcgtc acggatccgg ccgaacaaac tccggaggc agcgtgatgc       2880 ggcaacaatc acacggattt cccgtgaacg gtctgaatga gcggattatt ttcagggaaa     2940
gtgagtgtgg tcagcgtgca ggtatatggg ctatgatgtg cccggcgctt gaggcttt ct     3000 gcctcatgac gtgaaggtgg tttgttgccg tgttgtgtgg cagaaagaag atagccccgt     3060
agtaagttaa ttttcattaa ccaccacgag gcatccctat gtctagtcca catcaggata     3120
gcctcttacc gcgctttgcg caaggagaag aaggccatga aactaccacg aagttccctt     3180
gtctggtgtg tgttgatcgt gtgtctcaca ctgttgatat tcacttatct gacacgaaaa     3240
tcgctgtgcg agattcgtta cagagacgga cacagggagg tggcggcttt catggcttac     3300
gaatccggta agtagcaacc tagaggcggg cgcaggcccg ccttttcagg actgatgctg     3360
gtctgactac tgaagcgcct ttataaaggg gctgctggtt cgccggtagc ccctttctcc     3420
ttgctgatgt tgtgggaatt tcgagcaaga cgtttcccgt tgaatatggc tcataacacc     3480
ccttgtatta ctgtttatgt aagcagacag ttttattgtt catgatgata tattttatc     3540 ttgtgcaatg taacatcaga gattttgaga cacaacgtgg ctttcccccc cccccctgca     3600 gggggcgct gaggtctgcc tcgtgaagaa ggtgttgctg actcatacca ggcctgaatc      3660
gccccatcat ccagccagaa gtgagggagc cacggttgat gagagctttg ttgtaggtgg     3720
accagttggt gattttgaac ttttgctttg ccacggaacg gtctgcgttg tcgggaagat     3780
gcgtgatctg gggatcccca cgcgccctgt agcggcgcat taagcgcggc gggtgtggtg     3840
gttacgcgca gcgtgaccgc tacacttgcc agcgccctag cgcccgctcc tttcgctttc     3900
ttcccttcct ttctcgccac gttcgccggc tttccccgtc aagctctaaa tcggggcatc     3960
cctttagggt tccgatttag tgctttacgg cacctcgacc ccaaaaaact tgattagggt     4020
gatggttcac gtagtgggcc atcgccctga tagacggttt ttcgcccttt gacgttggag     4080
tccacgttct ttaatagtgg actcttgttc caaactggaa caacactcaa ccctatctcg     4140
gtctattctt ttgatttata agggattttg ccgatttcgg cctattggtt aaaaaatgag     4200
ctgatttaac aaaaatttaa cgcgaatttt aacaaaatat taacgtttac aatttcaggt     4260
ggcgaattcc ccggggaatt cacttttcgg ggaaatgtgc gcggaacccc tatttgttta     4320
tttttctaaa tacattcaaa tatgtatccg ctcatgagac aataaccctg ataaatgctt     4380
caataatatt gaaaaaggaa gagtatgagt attcaacatt tccgtgtcgc ccttattccc     4440
ttttttgcgg catttgcct tcctgttttt gctcacccag aaacgctggt gaaagtaaaa     4500
gatgctgaag atcagttggg tgcacgagtg ggttacatcg aactggatct caacagcggt     4560
aagatccttg agagttttcg ccccgaagaa cgttttccaa tgatgagcac ttttaaagtt     4620
ctgctatgtg gcgcggtatt atcccctatt gacgccgggc aagagcaact cggtcgccgc     4680
atacactatt ctcagaatga cttggttgag tactcaccag tcacagaaaa gcatcttacg     4740
gatggcatga cagtaagaga attatgcagt gctgccataa ccatgagtga taacactgcg     4800
gccaacttac ttctgacaac gatcggagga ccgaaggagc taaccgcttt tttgcacaac     4860
atgggggatc atgtaactcg ccttgatcgt tgggaaccgg agctgaatga agccatacca     4920
aacgacgagc gtgacaccac gatgcctgta gcaatggcaa caacgttgcg caaactatta     4980
actggcgaac tacttactct agcttcccgg caacaattaa tagactggat ggaggcggat     5040
```

```
aaagttgcag gaccacttct gcgctcggcc cttccggctg gctggtttat tgctgataaa    5100
tctggagccg gtgagcgtgg gtctcgcggt atcattgcag cactgggcc agatggtaag     5160
ccctcccgta tcgtagttat ctacacgacg gggagtcagg caactatgga tgaacgaaat    5220
agacagatcg ctgagatagg tgcctcactg attaagcatt ggtaactgtc agaccaagtt    5280
tactcatata tactttagat tgatttaaaa cttcattttt aatttaaaag gatctaggtg    5340
aagatccttt ttgataatct catgaccaaa atcccttaac gtgagttttc gttccactga    5400
gcgtcagacc ccgtagaaaa gatcaaagga tcttcttgag atcctttttt tctgcgcgta    5460
atctgctgct tgcaaacaaa aaaaccaccg ctaccagcgg tggtttgttt gccggatcaa    5520
gagctaccaa ctcttttttcc gaaggtaact ggcttcagca gagcgcagat accaaatact    5580
gtccttctag tgtagccgta gttaggccac cacttcaaga actctgtagc accgcctaca    5640
tacctcgctc tgctaatcct gttaccagtg gctgctgcca gtggcgataa gtcgtgtctt    5700
accgggttgg actcaagacg atagttaccg gataaggcgc agcggtcggg ctgaacgggg    5760
ggttcgtgca cacagcccag cttggagcga acgacctaca ccgaactgag atacctacag    5820
cgtgagctat gagaaagcgc cacgcttccc gaagggagaa aggcggacag gtatccggta    5880
agcggcaggg tcggaacagg agagcgcacg agggagcttc caggggggaaa cgcctggtat    5940
ctttatagtc ctgtcgggtt tcgccacctc tgacttgagc gtcgattttt gtgatgctcg    6000
tcagggggc ggagcctatg gaaaaacgcc agcaacgcgg ccttttttacg gttcctggcc    6060
ttttgctggc cttttgctca cat                                             6083
```

<210> SEQ ID NO 17
<211> LENGTH: 267
<212> TYPE: PRT
<213> ORGANISM: Artificial Sequence
<220> FEATURE:
<223> OTHER INFORMATION: scFv6 anti-CD3

<400> SEQUENCE: 17

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Leu Ala Arg Arg Gly Ala Ser Val Lys Met Ser Cys Lys Ala Ser Gly
        35                  40                  45

Tyr Thr Phe Thr Arg Tyr Thr Met His Trp Val Lys Gln Arg Pro Gly
    50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Ser Leu
        115                 120                 125

Asp Tyr Trp Gly Gln Gly Thr Thr Leu Thr Val Ser Ser Ala Lys Thr
    130                 135                 140

Thr Pro Asp Ile Val Leu Thr Gln Ser Pro Ala Ile Met Ser Ala Ser
145                 150                 155                 160

Pro Gly Glu Lys Val Thr Met Thr Cys Ser Ala Ser Ser Val Ser
                165                 170                 175
```

```
Tyr Met Asn Trp Tyr Gln Gln Lys Ser Gly Thr Ser Pro Lys Arg Trp
        180             185                 190

Ile Tyr Asp Thr Ser Lys Leu Ala Ser Gly Val Pro Ala His Phe Arg
        195             200                 205

Gly Ser Gly Ser Gly Thr Ser Tyr Ser Leu Thr Ile Ser Gly Met Glu
        210             215             220

Ala Glu Asp Ala Ala Thr Tyr Tyr Cys Gln Gln Trp Ser Ser Asn Pro
225             230             235                 240

Phe Thr Phe Gly Ser Gly Thr Lys Leu Glu Ile Asn Arg Ala Asp Thr
            245             250                 255

Ala Ala Ala Gly Ser His His His His His His
            260             265
```

The invention claimed is:

1. A method for immunotherapy comprising the step of administering to a subject a pharmaceutical composition comprising
(i) a bivalent diabody comprising a non-covalent dimer of single-chain Fv-antibodies each consisting essentially of a $V_H$ domain and a $V_L$ domain specific to human CD3, wherein the $V_H$ domain and the $V_L$ domain are covalently linked either without a linker or with a peptide linker, the bivalent diabody is characterized by the following features:
  (a) it is devoid of constant antibody domains;
  (b) it specifically binds to an epitope of human TCR/CD3 complex bivalently; and
  (c) it is capable of suppressing an immune reaction; and
(ii) a suitable pharmaceutical carrier, wherein said immunotherapy is a therapy against acute transplant rejections, type I diabetes, multiple sclerosis or rheumatoid arthritis.

2. A method for immunotherapy comprising the step of administering to a subject a pharmaceutical composition comprising
(i) a non-covalent dimer of single-chain Fv-antibodies (scFvs), each scFv with one $V_H$ domain and one $V_L$ domain specific to human CD3, wherein each $V_H$-$V_L$ pair is separated by a peptide linker or bound by a peptide bond, the non-covalent dimer of single-chain $F_v$-antibodies characterized by the following features:
  (a) it is devoid of constant antibody domains;
  (b) it specifically binds to an epitope of human TCR/CD3 complex bivalently;
  (c) it is capable of suppressing an immune reaction; and
(ii) a suitable pharmaceutical carrier, wherein said immunotherapy is a therapy against acute transplant rejections, type I diabetes, multiple sclerosis or rheumatoid arthritis.

3. The method according to claim 1 or 2, wherein the suitable pharmaceutical carrier is selected from the group consisting of an emulsion, a wetting agent and a sterile solution.

4. The method according to claim 1 or 2, wherein said immunotherapy is a therapy against acute transplant rejections.

5. The method according to claim 1 or 2, wherein the $V_H$ domain and the $V_L$ domain of the bivalent diabody are covalently linked via a peptide linker SAKTTP (SEQ ID NO:1).

6. The method according to claim 1 or 2, wherein the $V_H$ domain and the $V_L$ domain of the bivalent diabody correspond to the variable domains of an antibody produced by the hybridoma of ATCC deposit number CRL 8001.

* * * * *